US011925308B2

(12) United States Patent
Xu et al.

(10) Patent No.: US 11,925,308 B2
(45) Date of Patent: Mar. 12, 2024

(54) IONIZING RADIATION-FREE DENTAL IMAGING BY NEAR-INFRARED FLUORESCENCE, AND RELATED SYSTEMS

(71) Applicants: Jian Xu, Baton Rouge, LA (US);
Shaomian Yao, Baton Rouge, LA (US);
Zhongqiang Li, Baton Rouge, LA (US)

(72) Inventors: Jian Xu, Baton Rouge, LA (US);
Shaomian Yao, Baton Rouge, LA (US);
Zhongqiang Li, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 153 days.

(21) Appl. No.: 16/965,580

(22) PCT Filed: Feb. 15, 2019

(86) PCT No.: PCT/US2019/018327
§ 371 (c)(1),
(2) Date: Jul. 28, 2020

(87) PCT Pub. No.: WO2019/161284
PCT Pub. Date: Aug. 22, 2019

(65) Prior Publication Data
US 2021/0038065 A1 Feb. 11, 2021

Related U.S. Application Data

(60) Provisional application No. 62/631,558, filed on Feb. 16, 2018.

(51) Int. Cl.
*A61B 1/00* (2006.01)
*A61B 1/04* (2006.01)
(Continued)

(52) U.S. Cl.
CPC .. *A61B 1/000094* (2022.02); *A61B 1/000095* (2022.02); *A61B 1/00165* (2013.01);
(Continued)

(58) Field of Classification Search
None
See application file for complete search history.

(56) References Cited

U.S. PATENT DOCUMENTS 9,345,389 B2 * 5/2016 Nie .......................... G01J 3/44
11,308,355 B2 * 4/2022 Shah ...................... G06K 9/627
(Continued)

FOREIGN PATENT DOCUMENTS

WO 2017/174998 A1 10/2017

OTHER PUBLICATIONS

PCT/US2019/018327 International Search Report completed Apr. 12, 2019.
(Continued)

*Primary Examiner* — Ricky Chin
(74) *Attorney, Agent, or Firm* — Venable LLP; Keith G. Haddaway

(57) ABSTRACT

According to some embodiments of the invention, a near-infrared fluorescence endoscopic dental imaging system includes an endoscope forming a plurality of lumens therein; a spectrometer optically coupled to a first lumen of the endoscope; a near-infrared camera optically coupled to a second lumen of the endoscope; a data processor in communication with the spectrometer and the near-infrared camera; and a display system in communication with the data processor. The near-infrared camera is configured to capture a near-infrared two-dimensional dental image of a specimen and transmit the near-infrared two-dimensional dental image to the data processor. The spectrometer is configured to capture fluorescent light from the specimen
(Continued)

and provide a spectroscopic signal to the data processor. The display system is configured to communicate with the data processor to receive the near-infrared two-dimensional dental image and the spectroscopic signal and to display a two-dimensional dental image of the specimen.

18 Claims, 20 Drawing Sheets

(51) Int. Cl.

| | | |
|---|---|---|
| A61B 1/06 | (2006.01) | |
| A61B 1/07 | (2006.01) | |
| A61B 1/24 | (2006.01) | |
| A61B 5/00 | (2006.01) | |

(52) U.S. Cl.
CPC .......... *A61B 1/00186* (2013.01); *A61B 1/043* (2013.01); *A61B 1/046* (2022.02); *A61B 1/0638* (2013.01); *A61B 1/0646* (2013.01); *A61B 1/0669* (2013.01); *A61B 1/0684* (2013.01); *A61B 1/07* (2013.01); *A61B 1/24* (2013.01); *A61B 5/0071* (2013.01); *A61B 5/0075* (2013.01); *A61B 5/0088* (2013.01)

(56) References Cited

U.S. PATENT DOCUMENTS

| | | | |
|---|---|---|---|
| 2006/0158647 A1* | 7/2006 | Yao | G01J 3/027 356/326 |
| 2009/0237498 A1* | 9/2009 | Modell | A61B 1/045 348/E7.085 |
| 2009/0270702 A1* | 10/2009 | Zeng | G01N 21/4795 600/323 |
| 2010/0056928 A1* | 3/2010 | Zuzak | G01J 3/10 356/302 |
| 2010/0106025 A1* | 4/2010 | Sarfaty | G01J 3/0291 600/476 |
| 2010/0185067 A1* | 7/2010 | Gupta | G01J 3/1256 600/323 |
| 2011/0102566 A1* | 5/2011 | Zakian | A61B 5/0075 348/66 |
| 2011/0245602 A1 | 10/2011 | Brannon | |
| 2011/0280810 A1* | 11/2011 | Hauger | G02B 21/0052 424/9.6 |
| 2012/0271176 A1* | 10/2012 | Moghaddam | A61B 17/1703 600/476 |
| 2013/0033589 A1* | 2/2013 | Demos | A61B 1/063 348/E7.085 |
| 2013/0265568 A1* | 10/2013 | Micheels | G01N 21/3577 356/51 |
| 2014/0066712 A1* | 3/2014 | Robertson | B25B 13/08 600/109 |
| 2014/0303491 A1* | 10/2014 | Shekhar | A61B 8/587 600/424 |
| 2014/0316255 A1* | 10/2014 | Garai | A61B 34/20 600/478 |
| 2015/0010878 A1* | 1/2015 | Seibel | G01N 21/645 433/215 |
| 2015/0248770 A1* | 9/2015 | Hasegawa | G01N 21/4795 382/131 |
| 2015/0282749 A1* | 10/2015 | Zand | A61B 1/043 600/301 |
| 2016/0106868 A1* | 4/2016 | Hu | A61K 49/0032 424/9.6 |
| 2016/0239953 A1* | 8/2016 | Ngadi | G06V 10/764 |
| 2016/0278678 A1* | 9/2016 | Valdes | A61B 1/00009 |
| 2016/0331301 A1* | 11/2016 | Radmand | A61B 6/145 |
| 2017/0035281 A1* | 2/2017 | Takeuchi | G02B 27/4227 |
| 2017/0196643 A1* | 7/2017 | Popovic | A61B 34/30 |
| 2017/0322079 A1* | 11/2017 | Do | A61B 1/045 |
| 2018/0020922 A1* | 1/2018 | Liu | A61B 5/145 600/300 |
| 2018/0028065 A1* | 2/2018 | Elbaz | A61B 5/7203 |
| 2018/0247153 A1* | 8/2018 | Ganapati | A61B 5/0059 |
| 2019/0029522 A1* | 1/2019 | Sato | A61C 7/08 |
| 2019/0083159 A1* | 3/2019 | Hancock | A61B 18/1477 |
| 2019/0208998 A1* | 7/2019 | Powers | A61B 1/2736 |
| 2021/0038065 A1* | 2/2021 | Xu | A61B 1/043 |
| 2021/0056685 A1* | 2/2021 | Zhang | G06T 7/194 |
| 2021/0173120 A1* | 6/2021 | Peters | G01W 1/12 |
| 2021/0345870 A1* | 11/2021 | Xu | A61B 1/24 |

OTHER PUBLICATIONS

PCT/US2019/018327 Written Opinion completed Apr. 12, 2019.
Gonzales et al., "An in vivo 3D micro-CT evaluation of tooth movement after the application of different force magnitudes in rat molar", The Angle orthodontist, 2009, vol. 79, pp. 703-714.
Hsieh et al., "Dental optical coherence tomography", Sensors, 2013, vol. 13, pp. 8928-8949.
Kattainen et al., "In utero/lactational 2,3,7,8-tetrachlorodibenzo-p-dioxin exposure impairs molar tooth development in rats", Toxicol Appl Pharmacol., 2001, vol. 174, pp. 216-224.
Nakajima et al., "Development of three-dimensional FE modeling system from the limited cone beam CT images for orthodontic tipping tooth movement", Dent Mater J., 2007, vol. 26, pp. 882-891.
Schambach et al., "Application of micro-CT in small animal imaging", Methods, 2010, vol. 50, pp. 2-13.
Holdsworth et al., "Micro-CT in small animal and specimen imaging", Trends in Biotechnology, 2002, vol. 20, pp. S34- S39.
Badea et al., "In vivo small-animal imaging using micro-CT and digital subtraction angiography", Physics in medicine and biology, 2008, vol. 53, p. R319-R350.
Kosaka et al., "Near infrared fluorescence-guided real-time endoscopic detection of peritoneal ovarian cancer nodules using intravenously injected indocyanine green", International journal of cancer, 2011, vol. 129, pp. 1671-1677.
Xu et al., "Using Micro-Computed Tomography to Evaluate the Dynamics of Orthodontically Induced Root Resorption Repair in a Rat Model", PLoS One, 2016, 9 pages.
Alander et al., "A review of indocyanine green fluorescent imaging in surgery", International Journal of Biomedical Imaging, 2012, 26 pages.
Parthasarathy et al., "Intraoperative imaging of tumors with indocyanine green fluorescence with an endoscope". In SPIE BIOS: 93110X-93110X-93116. International Society for Optics and Photonics, 2015, 7 pages.
DSouza et al., "Review of fluorescence guided surgery systems: identification of key performance capabilities beyond indocyanine green imaging", Journal of Biomedical Optics, 2016, vol. 21, 16 pages.
Schmidt et al., "Feasibility of real-time near-infrared indocyanine green fluorescence endoscopy for the evaluation of mucosal head and neck lesions", Head Neck, 2017, vol. 39, pp. 234-240.
Maarek et al., "Measurement of cardiac output with indocyanine green transcutaneous fluorescence dilution technique", Anesthesiology, 2004, vol. 100, pp. 1476-1483.
Schaafsma et al., "The clinical use of indocyanine green as a near-infrared fluorescent contrast agent for image-guided oncologic surgery", J Surg Oncol., 2011, vol. 104, pp. 323-332.
Yokoyama et al., "A feasibility study of NIR fluorescent image-guided surgery in head and neck cancer based on the assessment of optimum surgical time as revealed through dynamic imaging", Onco Targets Ther., 2013, vol. 6, pp. 325-330.
Yokoyama et al., "Impact of Endoscopic Indocyanine Green Fluorescence Imaging on Superselective Intra-arterial Chemotherapy for Recurrent Cancer of the Skull Base", Anticancer Res., 2016, vol. 36, pp. 3419-3424.
Plante et al., "Sentinel node mapping with indocyanine green and endoscopic near-infrared fluorescence imaging in endometrial cancer. A pilot study and review of the literature", Gynecol Oncol., 2015, vol. 137, pp. 443-447.
Huang et al., "Endoscopically-assisted operations in the treatment of odontogenic peripheral osteomyelitis of the posterior mandible", The British journal of oral & maxillofacial surgery, 2016, vol. 54, pp. 542-546.

(56) References Cited

OTHER PUBLICATIONS

Shah et al., "Recent advances in imaging technologies in dentistry", World journal of radiology, 2014, vol. 6, Issue 10, pp. 794-807.
Vandenberghe et al., "Modern dental imaging: a review of the current technology and clinical applications in dental practice", Eur. Radiol., 2010, vol. 20, pp. 2637-2655.
Cox et al., "Imaging techniques: Super-resolution ultrasound", Nature, 2015, vol. 527, pp. 451-452.
Marotti et al., "Recent advances of ultrasound imaging in dentistry-a review of the literature", Oral surgery, oral medicine, oral pathology and oral radiology, 2013, vol. 115, No. 6, pp. 819-832.
Fujimoto "Optical coherence tomography for ultrahigh resolution in vivo imaging", Nature biotechnology, 2003, vol. 21, No. 11, pp. 1361-1367.
Wojtkowski et al., "Three-dimensional retinal imaging with high-speed ultrahigh-resolution optical coherence tomography", Ophthalmology, 2005, vol. 112, No. 10, pp. 1734-1746.
Lungova et al., "Tooth-bone morphogenesis during postnatal stages of mouse first molar development",J Anat., 2011, vol. 218, pp. 699-716.
Abdelwahab et al., "Endoscopic enucleation of large jaw cysts: Promising outcomes", Auris Nasus Larynx, (2018), vol. 45, pp. 578-584.
Smith et al., "Bioimaging: second window for in vivo imaging", Nat. Nanotechnol., 2009, vol. 4, No. 11, pp. 710-711.
Weissleder "A clearer vision for in vivo imaging", Nat. Biotechnol., 2001, vol. 19, pp. 316-317.
Frangioni "In vivo near-infrared fluorescence imaging", Curr. Opin. Chem. Biol., 2003, vol. 7, pp. 626-634.
Mohs et al., "Hand-held spectroscopic device for in vivo and intraoperative tumor detection: contrast enhancement, detection sensitivity, and tissue penetration", Anal. Chem., 2010, 9058-9065.
Fleischmannova et al., "Mouse models of tooth abnormalities", Eur. J. Oral Sci., vol. 116, pp. 1-10.
Wise et al., "Changes in the tartrate-resistant acid phosphatase cell population in dental follicles and bony crypts of rat molars during tooth eruption", Journal of dental research, 1989, vol. 68, pp. 150-156.
Yoneda et al., "Development of a root canal treatment model in the rat.", Sci Rep., 2017, vol. 7, (9 pages).
Bühler et al., "Imaging of occlusal dental caries (decay) with near-IR light at 1310-nm", Optics Express, (2005), vol. 13, No. 2, pp. 573-582.
Lyngstadaas et al., "Crown morphology, enamel distribution, and enamel structure in mouse molars", Anat Rec., (1998), vol. 250, pp. 268-280.
Anand et al., "Cancer is a preventable disease that requires major lifestyle changes", Pharm. Res., (2008), vol. 25, No. 9, pp. 2097-2116.
Lin et al., "Radiation risk from medical imaging". In Mayo Clin. Proc., (2010), vol. 85, pp. 1142-1146.
De González et al., "Projected cancer risks from computed tomographic scans performed in the United States in 2007", Arch. Intern. Med., (2009), vol. 169, No. 22, pp. 2071-2077.
Brenner et al., "Computed tomography—an increasing source of radiation exposure", N. Engl. J. Med., (2007), vol. 357, pp. 2277-2284.
Association, A.D. 2012. Dental radiographic examinations: recommendations for patient selection and limiting radiation exposure. Chicago: ADA.
"Health risks from exposure to low levels of ionizing radiation: BEIR VII phase 2" National Research Council (National Academies Press, 2006).
Fujiwara et al., "Sentinel lymph node detection in skin cancer patients using real-time fluorescence navigation with indocyanine green: preliminary experience", Journal of Plastic, Reconstructive & Aesthetic Surgery, (2009), vol. 62: e373-e378.
Sener et al., "Non-Syndromic Familial Unerupted Teeth: A Rare Contidion", Cumhuriyet Dental Journal, (2013), vol. 18, Issue 4, pp. 359-363.
Pereira et al., "Taking advantage of an unerupted third molar: a case report", Dental Press J Orthod., (2017), vol. 22, pp. 97-101.
Shah et al., "A. Recent advances in imaging technologies in dentistry", World J Radiol., (2014), vol. 6, pp. 794-807.
Kiljunen et al., "Dental cone beam CT: A review", Phys Med., (2015), vol. 31, pp. 844-860.
Hsieh et al., "Dental optical coherence tomography", Sensors (Basel), (2013), vol. 13, pp. 8928-8949.
Metsala et al., "Quality assurance in digital dental imaging: a systematic review", Acta Odontol Scand., (2014), vol. 72, pp. 362-371.
Valentin et al., "The 2007 recommendations of the international commission on radiological protection", Annals of the ICRP, Publication 103, (2012), (328 pages).
Bolouri et al., "Performance of orthopantomography, planar scintigraphy, CT alone and SPECT/CT in patients with suspected osteomyelitis of the jaw", European journal of nuclear medicine and molecular imaging, (2013), vol. 40, pp. 411-417.
Adeyemo et al., "A systematic review of the diagnostic role of ultrasonography in maxillofacial fractures", International journal of oral and maxillofacial surgery, (2011), vol. 40, pp. 655-661.
Alander et al., "A review of indocyanine green fluorescent imaging in surgery", Int J Biomed Imaging, (2012), vol. 2012, Article 940585, (26 pages).
Parthasarathy et al., "Intraoperative imaging of tumors with indocyanine green fluorescence with an endoscope", Proceedings of SPIE, (2015), vol. 9311, (7 pages).
Simon et al., "Near-infrared imaging of secondary caries lesions around composite restorations at wavelengths from 1300-1700-nm", Dental Materials, (2016), vol. 32, 587-595.
Chung et al., "Near infrared imaging of teeth at wavelengths between 1200 and 1600 nm", Proceedings of SPIE, (2011), vol. 7884, (8 pages).
Li et al., "Endoscopic near-infrared dental imaging with indocyanine green: a pilot study", Annals of the New York Academy of Sciences, (2018), vol. 1421, pp. 88-96.
DSouza et al., "Review of fluorescence guided surgery systems: identification of key performance capabilities beyond indocyanine green imaging", J Biomed Opt., (2016), vol. 21, No. 8, (16 pages).
Xu et al. , "New horizons in intraoperative diagnostics of cancer in image and spectroscopy guided pancreatic cancer surger", New Horizons in Clinical Case Reports, (2017), vol. 1. (2 pages).
Xu et al., "Nanofluorophore Assisted Fluorescence Image-guided Cancer Surgery", Journal of Medical—Clinical Research & Reviews, (2018), Volssue 1, pp. 1-3.
Boehm et al., "Diode Laser Activated Indocyanine Green Selectively Kills Bacteria", J Int Acad Periodontol., (2011), vol. 13,(8 pages).
McNally et al., "Dye-assisted diode laser ablation of carious enamel and dentine", Aust Dent J., (1999), vol. 44, No. 3, pp. 169-175.
Huang et al., "Endoscopically-assisted operations in the treatment of odontogenic peripheral osteomyelitis of the posterior mandible", Br J Oral Maxillofac Surg., (2016), vol. 54, pp. 542-546.
Wise et al., "Changes in the tartrate-resistant acid phosphatase cell population in dental follicles and bony crypts of rat molars during tooth eruption", Journal of Dental Research, (1989), vol. 68, Issue 2, pp. 150-156.
Fleischmannova et al., "Mouse models of tooth abnormalities", Eur J Oral Scl., (2008), vol. 116, pp. 1-10.
Bodner et al., "Image accuracy of plain film radiography and computerized tomography in assessing morphological abnormality of impacted teeth", American Journal of Orthodontics and Dentofacial Orthopedics, (2001), vol. 120, pp. 623-628.
Smith et al., "Bioimaging: second window for in vivo imaging", Nat. Nanotechnol., (2009), vol. 4, pp. 710-711.
Desmettre et al., "Fluorescence properties and metabolic features of indocyanine green (ICG) as related to angiography", Survey of ophthalmology, (2000), vol. 45, pp. 15-27.
Kochubey et al., "Spectral characteristics of indocyanine green upon its interaction with biological tissues", Optics and Spectroscopy, (2005), vol. 99, pp. 560-566.

(56) References Cited

OTHER PUBLICATIONS

Santos Junior et al., "Are there hidden caries or is this another limitation of the diagnostic conventional exams", Revista Odonto Ciência, (2015), vol. 30, No. 2, p. 45-50.
Choo-Smith et al., "Shedding new light on early caries detection", Journal (Canadian Dental Association), (2008), vol. 74, pp. 913-918.

\* cited by examiner

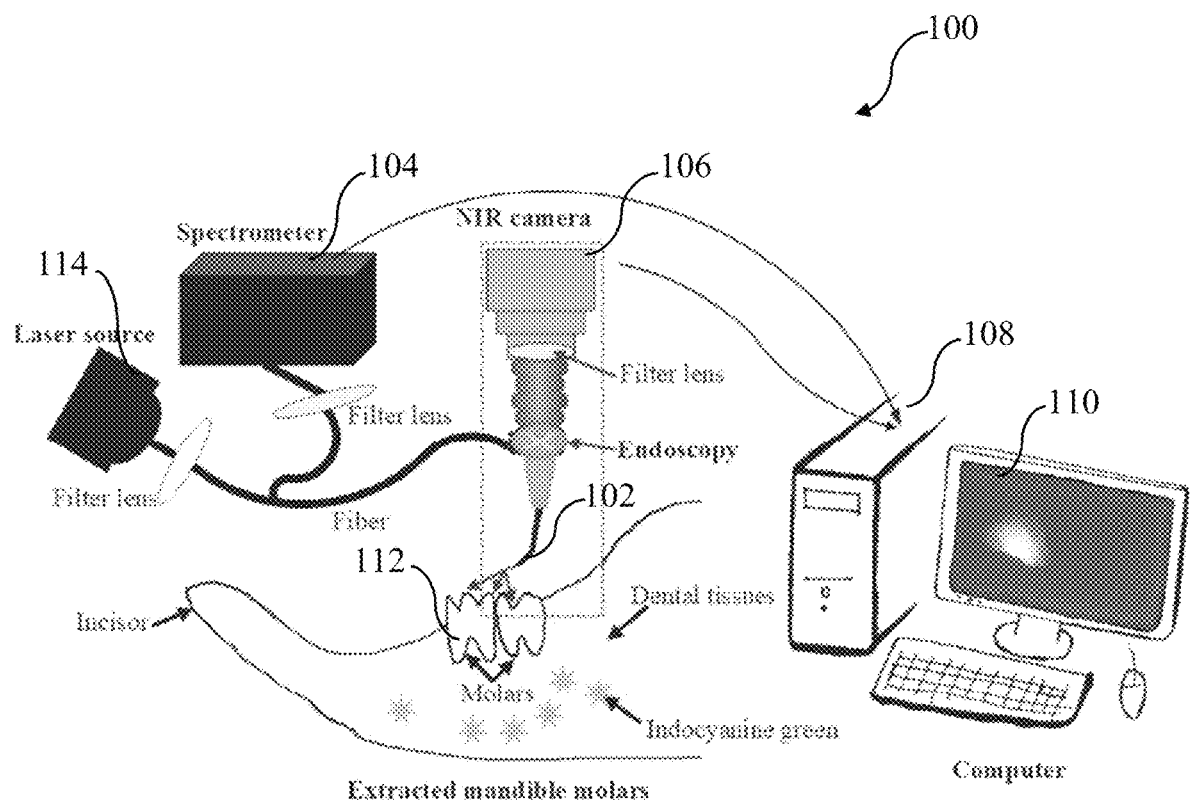
FIG. 1
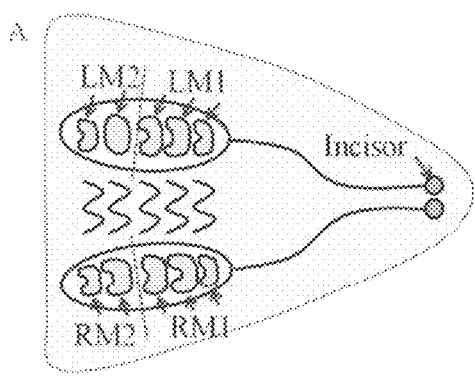 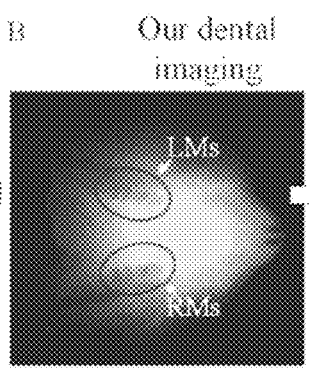 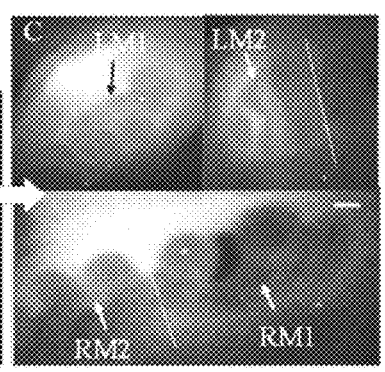
FIG. 2A  FIG. 2B  FIG. 2C

IONIZING RADIATION-FREE DENTAL IMAGING BY NEAR-INFRARED FLUORESCENCE, AND RELATED SYSTEMS

BACKGROUND

1. Technical Field

Embodiments of the invention relate generally to dental imaging, and more particularly, to systems and methods for ionizing radiation-free dental imaging by near-infrared fluorescence.

2. Discussion of Related Art

Dental imaging plays critical roles in dental clinics for diagnosis and surgeries. X-ray based imaging techniques, such as simple periapical 2D (2 dimension) X-ray and CT (Computed Tomography, including tuned aperture CT (TACT) and cone beam CT (CBCT)), are currently used in dental clinics.[1,2] Although those methods can achieve clear anatomical dental images,[3-6] there are several significant drawbacks, including exposing patients to ionizing radiation[5-8] and incapability of real-time observation[5,6]. When using micro-CT to assess dental structure in animal studies, animals usually have to be sacrificed at a particular time point, and obtained results are discontinuous and stationary.[9] Therefore, systems and methods are needed for cost-efficient, safe, and easy-to-use dental imaging that can be used for diagnosis of dental diseases and for real-time observation to guide dental surgeries.

SUMMARY

According to some embodiments of the invention, a near-infrared endoscopic dental imaging system includes an endoscope forming a plurality of lumens therein; a spectrometer optically coupled to a first lumen of the endoscope; a near-infrared camera optically coupled to a second lumen of the endoscope; a data processor in communication with the spectrometer and the near-infrared camera; and a display system in communication with the data processor. The near-infrared camera is configured to capture a near-infrared two-dimensional dental image of a specimen and transmit the near-infrared two-dimensional dental image to the data processor. The spectrometer is configured to capture fluorescent light from the specimen and provide a spectroscopic signal to the data processor. The display system is configured to communicate with the data processor to receive the near-infrared two-dimensional dental image and the spectroscopic signal and to display a two-dimensional dental image of the specimen.

According to some embodiments, the near-infrared endoscopic dental imaging system does not use ionizing-radiation materials. According to some embodiments, the near-infrared endoscopic dental imaging system includes a near-infrared illumination source optically coupled to the first lumen of the endoscope. According to some embodiments, the near-infrared illumination source comprises a laser diode. According to some embodiments, the near-infrared illumination source comprises a light emitting diode (LED).

According to some embodiments, the near-infrared endoscopic dental imaging system includes a bifurcated fiber disposed in the second lumen, the bifurcated fiber having a first channel optically coupled to the spectrometer and a second channel optically coupled to a near-infrared illumination source. According to some embodiments, the near-infrared camera is further configured to capture a two-dimensional dental video, and the display system is configured to display the two-dimensional dental video in real time.

According to some embodiments of the invention, a method for near-infrared endoscopic dental imaging includes administering a near-infrared fluorescent dye to a subject; waiting a predetermined period of time; illuminating the subject with near-infrared light; capturing a two-dimensional near-infrared dental image of the subject; capturing near-infrared light from the subject and analyzing the near-infrared light to create a spectroscopic signal; and displaying a two-dimensional near-infrared dental image.

According to some embodiments, the method includes displaying spectroscopic data corresponding to the spectroscopic signal. According to some embodiments, the method does not use ionizing-radiation materials. According to some embodiments, the method further includes capturing a two-dimensional near-infrared dental movie of the subject; and displaying the two-dimensional near-infrared dental movie of the subject in real time. According to some embodiments, the method includes analyzing the spectroscopic signal to identify one of inflammation or disease in imaged tissue.

According to some embodiments of the invention, a near-infrared dental imaging system includes a bifurcated optical fiber adapted to be disposed in a first lumen of an endoscope, and a spectrometer optically coupled to a first channel of the bifurcated optical fiber. The system also includes a near-infrared camera optically coupled to a second lumen of the endoscope, and a data processor in communication with the spectrometer and the near-infrared camera. The bifurcated optical fiber is configured to receive fluorescent light from a specimen into the first channel and transmit the fluorescent light to the spectrometer. The spectrometer is configured to detect the fluorescent light from the bifurcated optical fiber and provide a spectroscopic signal to the data processor. The near-infrared camera is configured to receive near-infrared light from the second lumen of the endoscope and capture a near-infrared two-dimensional dental image of the specimen. The near-infrared camera is further configured to transmit the near-infrared two-dimensional dental image to the data processor, and the data processor is configured to communicate with a display system to display a two-dimensional dental image of the specimen.

According to some embodiments of the invention, the near-infrared dental imaging system does not use ionizing-radiation materials. According to some embodiments, the system further includes a near-infrared illumination source optically coupled to a second channel of the bifurcated optical fiber. According to some embodiments, the near-infrared illumination source comprises a laser diode. According to some embodiments, the near-infrared illumination source comprises a light emitting diode (LED).

According to some embodiments of the invention, the near-infrared camera is further configured to capture a two-dimensional dental video, and the processor is configured to communicate with the display system to display the two-dimensional dental video in real time. According to some embodiments, the system includes a display system in communication with the processor, wherein the processor is configured to communicate with the display system to display a two-dimensional dental image of the specimen. According to some embodiments, the system includes an endoscope, wherein the bifurcated optical fiber is disposed in a first lumen of the endoscope, and the near-infrared camera is optically coupled to a second lumen of the endoscope.

BRIEF DESCRIPTION OF THE DRAWINGS

Further objectives and advantages will become apparent from a consideration of the description, drawings, and examples.

FIG. 1 shows an endoscopic NIR fluorescence dental imaging system according to some embodiments of the invention;

FIG. 2A shows dental structures (not drawn to scale), e.g. molars, that are imaged with the dental imaging system according to some embodiments;

FIG. 2B shows an occlusal view of the left molars (LMs) and right molars (RMs) captured by the dental imaging system according to some embodiments;

FIG. 2C shows a zoom-in view of the left molars 1 and 2 (LM1, LM2) and right molars 1 and 2 (RM1, RM2). Scale bar: 1 mm.

DETAILED DESCRIPTION

Figure 3:
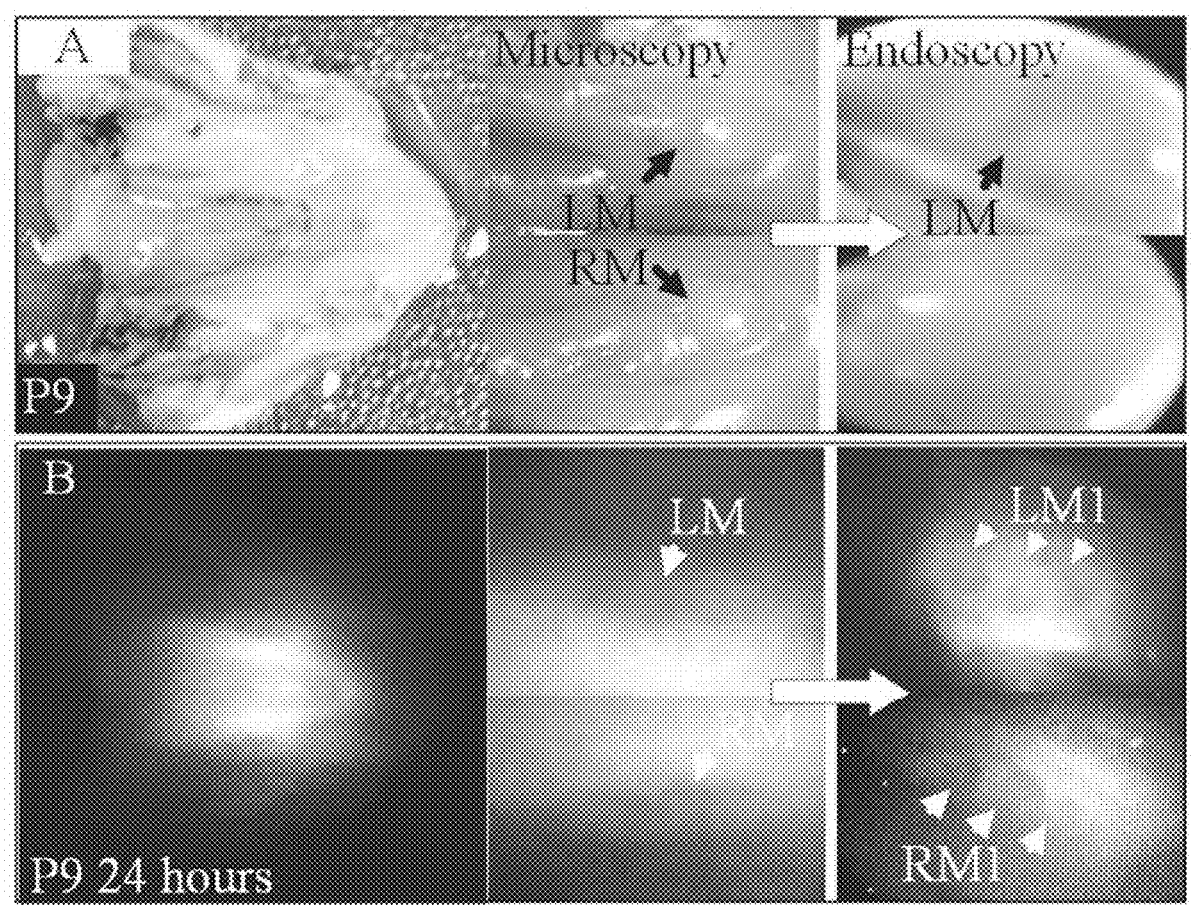
FIG. 3 shows bright field and NIR tooth images for the molar prior to eruption, acquired from P9 rats sacrificed after 24 hours of injection. (A) The bright-field images of P9 rat taken by microscopy and endoscopy. (B) The fluorescence images of P9 rat molars, without and with endoscopy. Excitation: 785 nm laser diode (LD).

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Current dental diagnosis largely relies on ionizing-radiation X-ray based imaging, but this technique suffers from complicated operations and exposes patients to ionizing radiation. According to the existing studies, dental radiography accounts for nearly one third of the total number of radiological examinations in USA and European Countries. This is because tooth imaging plays essential roles in dental research and clinics, including diagnosis and surgeries. Described herein is an efficient, sensitive, ionizing-radiation-free, and easy-to-use solution for dental imaging. Postnatal rats at different ages were injected with indocyanine green and molars were imaged by an endoscopic near-infrared fluorescence dental imaging system. The results indicate that near-infrared dental imaging can be used to observe the morphology of postnatal rat molar, especially at the early postnatal stages when the morphology cannot be identified under visible conditions. Small abnormal cusps can be observed by the imaging system disclosed herein and distinguished from the normal cusps of the molars. The imaging window can be realized as short as 10 minutes (after the injection of indocyanine green) for unerupted molars of postnatal days 14; 24 hours currently appear to be an optimized imaging window for the different postnatal rats. Overall, the endoscopic near-infrared fluorescence dental imaging not only has the potential to play significant roles in dental research, but also can serve as a safe and real-time imaging tool in dental diagnosis and treatment (surgeries). In addition, due to the intrinsic properties of near-infrared imaging, i.e. less tissue scattering and absorption, the systems and methods described herein can be used to image the deep (~10 mm beneath the surface) dental anatomical structures, which cannot be observed by traditional bright field imaging.

Fluorescence imaging plays essential roles in many areas of biomedical sciences, owing to its high contrast, high sensitivity, affordable cost and easy-to-use approach.[10, 11] Particularly, indocyanine green (ICG) is known to produce near-infrared fluorescence in ophthalmic angiography;[10, 12] it has been approved by Food and Drug Administration (FDA) and European Medicines Agency for clinical applications.[13] Nowadays, ICG has been widely used in the fields of retinal angiography, cardiac output monitoring, and cancer surgical imaging.[10, 12-17] As for ICG-based cancer imaging, the endoscope can significantly help to acquire more useful information, like the feeding artery to tumors, than wide-field imaging system.[11, 13, 17, 18] As for the endoscope on dentistry, an existing study indicated that endoscope, with visible (VIS) light illumination, can facilitate the surgery for removing the residual roots and can help to reduce pain and improve patient recovery from the surgery.[19]

ICG-based imaging in combination with an endoscope for near-infrared (NIR) dental imaging has not been reported. Described herein are systems and methods used to obtain NIR dental imaging on postnatal rats as a model animal, and to characterize ICG for the dental imaging contrast agent. A near-infrared dental imaging system (including both camera and spectroscopic devices) is used together with indocyanine green (ICG, FDA approved) as the fluorescence dye, to continuously monitor tooth development in an ionizing-radiation-free way. The results indicate that endoscopic NIR fluorescence dental imaging can serve as a significant and alternative tool for diagnosis of dental diseases and disorders. Endoscopic NIR dental imaging possesses complementary advantages to the current histology and X-ray imaging methods.[6] Importantly, endoscopic NIR fluorescence dental imaging can be used to observe dental tissues in real-time, making it a possible technique for guiding dental surgeries.

FIG. 1 shows a near-infrared endoscopic dental imaging system 100 according to some embodiments of the invention. The system 100 includes an endoscope 102 forming a plurality of lumens therein, and a spectrometer 104 optically coupled to a first lumen of the endoscope 102. The system 100 further includes a near-infrared camera 106 optically coupled to a second lumen of the endoscope 102. The system 100 includes a data processor 108 in communication with the spectrometer 104 and the near-infrared camera 106, and a display system 110 in communication with the data processor 108. The near-infrared camera 106 is configured to capture a near-infrared two-dimensional dental image of a specimen 112 and transmit the near-infrared two-dimensional dental image to the data processor 108. The spectrometer 104 is configured to capture fluorescent light from the specimen 112 and provide a spectroscopic signal to the data processor 108. The display system 110 is configured to communicate with the data processor 108 to receive the near-infrared two-dimensional dental image and the spectroscopic signal and to display a two-dimensional dental image of the specimen 112.

According to some embodiments of the invention, the near-infrared endoscopic dental imaging system 100 does not use ionizing-radiation materials. According to some embodiments, the system 100 further includes a near-infrared illumination source 114 optically coupled to the first lumen of the endoscope 102. According to some embodiments, the near-infrared illumination source 114 includes a laser diode. According to some embodiments, the near-infrared illumination 114 source includes a light emitting diode (LED).

Figure 8:
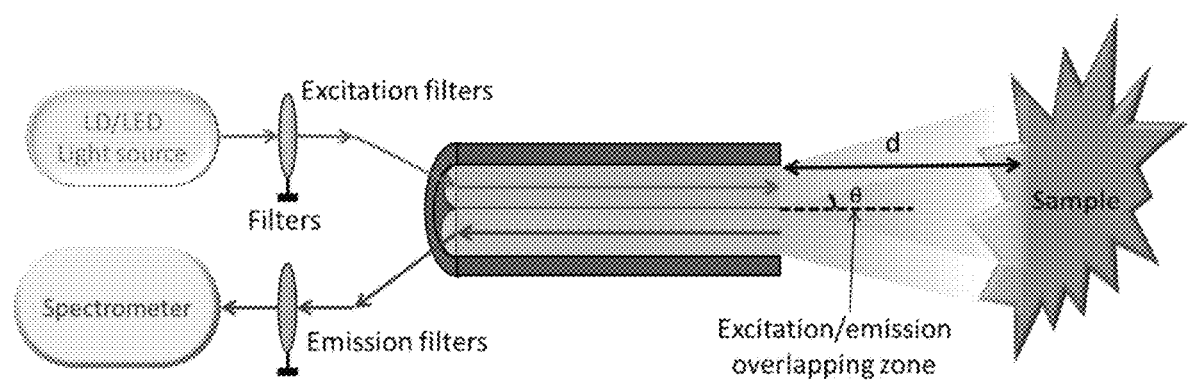
FIG. 8 shows a bifurcated fiber optic design showing the optical path, the excitation (top) and collection/emission (bottom) channels. θ: the maximum acceptance angle. The bifurcated fiber is coupled to the spectrometer, and can provide the excitation light for the imaging from both the camera and the spectrometer.

According to some embodiments of the invention, the near-infrared endoscopic dental imaging system 100 includes a bifurcated fiber disposed in the second lumen, the bifurcated fiber having a first channel optically coupled to the spectrometer 104 and a second channel optically coupled to a near-infrared illumination source 114. An example of a bifurcated fiber is shown in FIG. 8. According to some embodiments, the near-infrared camera 106 is further configured to capture a two-dimensional dental video, and the display system 110 is configured to display the two-dimensional dental video in real time.

According to some embodiments of the invention, a method for near-infrared endoscopic dental imaging includes administering a near-infrared fluorescent dye to a subject, waiting a predetermined period of time, and illuminating the subject with near-infrared light. According to some embodiments, the near-infrared fluorescent dye is administered intradermally, intraorally (like mouthwash), or intravenously. For example, the patient may take the near-infrared fluorescent dye solution (for example, ICG solution) as they would take a mouthwash or oral rinse; just like the mouthwash procedure, the dye can be spit out afterwards. The dye solution is compatible to human body (FDA approved dye), and thus the patient can swallow the dye solution as well if they choose to do so. The predetermined time may be, for example, 10 minutes, 1 hour, 12 hours, 24 hours, or 72 hours. These times are provided as examples, and the embodiments of the invention are not limited to these times.

The method further includes capturing a two-dimensional near-infrared dental image of the subject, capturing near-infrared light from the subject and analyzing the near-infrared light to create a spectroscopic signal, and displaying a two-dimensional near-infrared dental image.

According to some embodiments, the method further includes displaying spectroscopic data corresponding to the spectroscopic signal. According to some embodiment, the method does not use ionizing-radiation materials. According to some embodiments, the method further includes capturing a two-dimensional near-infrared dental movie of the subject, and displaying the two-dimensional near-infrared dental movie of the subject in real time. According to some embodiments, the method further includes analyzing the spectroscopic signal to identify one of inflammation or disease in imaged tissue.

Reagents and Animals

ICG, bovine serum albumin (BSA, 96%), phosphate buffered saline (PBS) were purchased from Sigma-Aldrich (St. Louis, MO). Ultrapure water (18.2 MΩ) was used to prepare the reagents. ICG powder was dissolved in ultrapure water with the maximum solubility (1 mg/mL) and BSA was dissolved in PBS to prepare 4% BSA/PBS solution. To investigate the sensitivity of the imaging system, ICG solution was diluted in BSA solution to concentrations ranging from 1 fM to 1 μM, and the sensitivity of the imaging system is up to 0.1 pM. Sprague Dawley rats were used. All animal experiments were approved by the Institutional Animal Care and Use Committee (IACUC) of Louisiana State University (USA) and were in accordance with the ethical guidelines for animal care.

To perform endoscopic NIR fluorescence dental imaging on developing molars, postnatal rats were administered an intradermal injection of ICG (5 mg/kg) from the backside at the postnatal (P) days 9 (P9), 14 (P14), 18 (P18), and 21 (P21). The intradermal injection can avoid ICG being quickly extracted by the liver.

Endoscopic NIR Fluorescence Dental Imaging System

To image the rat molar in different postnatal periods with NIR fluorescence, an endoscopic NIR fluorescence dental imaging system was designed in this study, as shown in FIG. 1. The system includes an NIR laser diode (LD, Turnkey Raman Lasers-785 Series; Ocean Optics, Inc.), an NIR camera (Guppy F038B; Allied Vision Technologies GmbH), a spectrometer (QEPro; Ocean Optics, Inc.), an endoscope (OSF-3; Olympus Corporation), and two filter lenses (Thorlabs Inc). One bifurcated fiber was employed to transfer the laser to the dental tissues and collect and send the fluorescence photons to the spectrometer. The spectrometer and NIR camera may be in communication with a data processor, such as a computer, for example. The data processor may be in communication with a display system, such as a monitor, for example. The specific components described herein are provided as examples. The embodiments of the invention are not limited to these specific examples.

Figure 7:
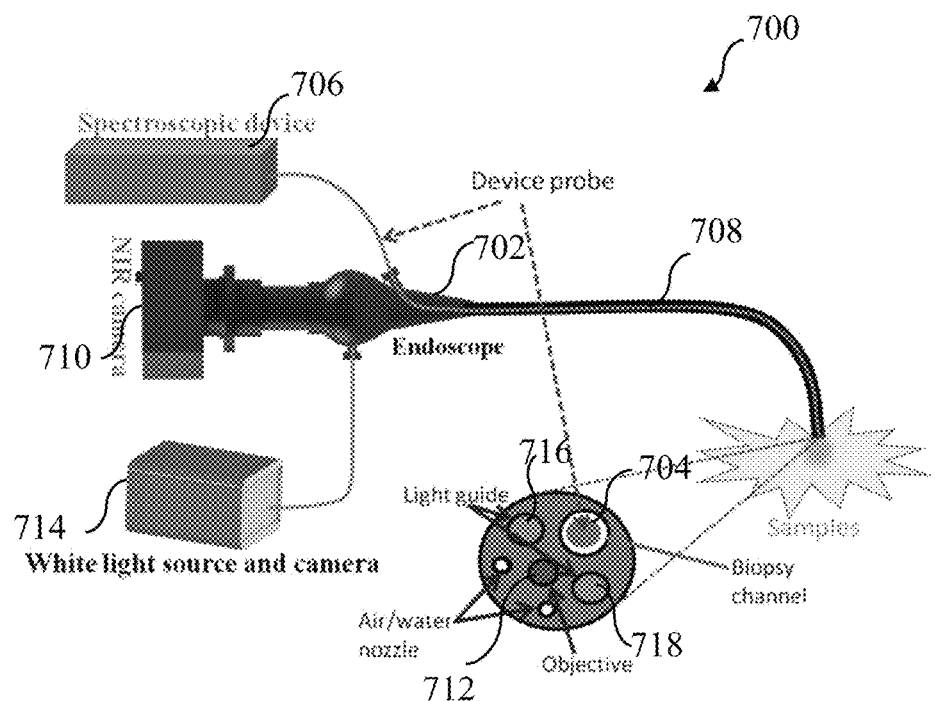
FIG. 7 shows a schematic diagram of the dental imaging system according to some embodiments, integrated with an endoscope.

FIG. 7 shows a schematic diagram of the dental imaging system according to some embodiments, integrated with an endoscope. The endoscope forms a plurality of lumens, at least a first of which is optically coupled to the spectrometer, and a second of which is optically coupled to the NIR camera. A white light source or white light video camera may also be coupled to one or more of the lumens.

FIG. 8 shows a bifurcated fiber optic design showing the optical path, and the excitation (top) and collection/emission (bottom) channels. θ represents the maximum acceptance angle. Light emitted from an NIR laser diode (LD) or NW light emitting diode (LED) travels through excitation fiber and illuminates the sample. The light emitted by the sample travels through the emission fiber and is collected by the spectrometer. The spectrometer may send a spectroscopic signal to the data processor.

The NIR camera and the spectrometer each have their own advantages, which can be complementary to each other. The NIR camera provides a direct overview of the imaging field, but with limited detection sensitivity; the spectrometer, although lacking capability of overview, provides the wavelength-resolved spectroscopy of each imaged point. The wavelength-resolved spectroscopy can provide much higher detection sensitivity (3~4 times better, i.e. it may identify the dental structures even if they are too low in fluorescence to be identified by the camera), more quantitative information, more precise background subtraction than the NIR camera, and novel spectroscopic signatures of tissues.

This unique feature enables quantitative studies by spectrometer. First, spectroscopic signals can be used to quantitatively estimate the ICG distributions in various tissues, which in turn helps to develop the best imaging strategies (e.g., ICG injection dosage, injection method, and imaging window) for dental patients in the form of "personalized medicine." For instance, in FIG. 6 (using the quantitative information extracted from the spectroscopy), although injected with same initial dosage of ICG, rats at different ages have different ICG accumulation at their molars (40~90 nM). This feature helps to understand the drug/dye biodistribution and dental tissue uptake associated with their individual differences (age difference in this case). Imaging strategies may be customized for individual patients.

Second, this feature also helps to discover the structural changes in the tissues, such as inflammation or disease. The recorded spectra may reveal the nuance of different fluorescence spectra, such as the peak wavelength shifts or waveform shapes, from the normal tissue and the tissue with infection, which may not be identified by the current camera imaging systems, as intrinsically the cameras can only output single fluorescence intensity. This feature may yield insight into understanding the microenvironment change, such as blood vessel growing, pH and fluorophore accumulation levels, at the different tissues. This microenvironment difference may be associated with structure changes of the tissues, including but not limited to infection or other dental diseases.

As shown in FIGS. 1 and 8, the system according to some embodiments includes a plurality of filters. The main function of the filters is to improve the detection sensitivity. Although ICG is an FDA-approved NIR dye, it is not a dye with great optical properties for the following reasons: (a) the emission peak and the excitation peak of ICG is very close to each other (less than 40 nm away); (b) ICG has poor quantum efficiency (how much absorbed excitation photons can induce emission photons; ICG: 0.3%~1.2%). A common issue of interfering the ICG detection is that the tail of excitation light is so strong that it completely covers the ICG emission signal. Therefore, we put one excitation filter (usually a band pass (~785 nm) or short pass filter) to cut off the tail of excitation light, and we put another emission filter (a long pass filter (>800 nm)) to further remove the undesired low wavelength light directly and indirectly (e.g., from the light scattering by the imaged tissues) from the excitation light source.

To capture images, the mandible molars were exposed by the 785 nm laser from the top orientation. To acquire NIR fluorescence images, the camera was ~30 cm away from the molar sample, while the endoscope in combination with the NIR camera was ~4 mm to acquire the endoscopic fluorescence images.

Results

NIR Imaging of the Rat Molars

An endoscopic NIR fluorescence dental imaging system was designed for real-time fluorescence imaging and tissue diagnosis in dentistry. This imaging method is based on NIR emission (650-950 nm), which does not involve any ionizing radiation risk to the patients, a major advantage compared to the prevalent dental X-ray imaging.[20, 21] This system comprises a NIR camera with moderate resolution (768×494 px) and a spectroscopic device. In the animal model experiments, this imaging system was assembled into a commercial endoscope (Olympus OSF-3, FIG. 1) and successfully imaged the rat dental structures with ICG injection (FIGS. 2A-2C).

The imaging system clearly imaged the rat dental anatomical structures, including the left and right molars (grinding teeth), in an occlusal view (FIGS. 2B, 2C); the buccal and lingual cusps (the small branched features on each tooth surface) of the molars were clearly recognized, with the resolution of ~100 μm, which is much higher than that of ultrasound imaging (sub-mm).[22, 23] The system is also capable of taking videos at 30 frames per second (FPS), i.e. in real-time, a unique advantage that is impossible with the prevalent X-ray[20, 21] and the OCT (optical coherence tomography)[2, 24, 25] dental imaging methods.

NIR Fluorescence Dental Imaging of the Molar Prior to Eruption

The eruption of rat molars usually starts from postnatal days 18.[26] Imaging the molar structure before eruption is challenging for the current bright-field approach.[2, 27] For instance, before the tooth eruption, the molars of P9 rats (FIG. 3, panel A) are buried inside alveolar bone and cannot be identified by the regular bright-field imaging. However, using the NIR fluorescence dental imaging system, three cusps of P9 rat Molar 1 (sacrificed after 24 hours of injection) can be clearly recognized from the surrounding dental tissues, especially from the endoscopic fluorescent images (FIG. 3, panel B). The system can image the dental anatomical structures deeply under the oral surface tissues, which is a unique advantage compared to the bright-field imaging[20, 21, 23] and OCT.[2, 24, 25] This advantage comes from the intrinsic properties of NIR imaging. In this imaging range, light has lower absorption by blood, water, and lipids;[28-30] therefore, the signal-to-noise ratio in imaging is greatly enhanced, while the autofluorescence is minimized.[28-30] The tissue penetration of light can be as good as 1-2 cm,[28-31] which can help to detect the dental tissues underneath the surface.

NIR Fluorescence Dental Imaging for the Erupted Molar

Figure 4:
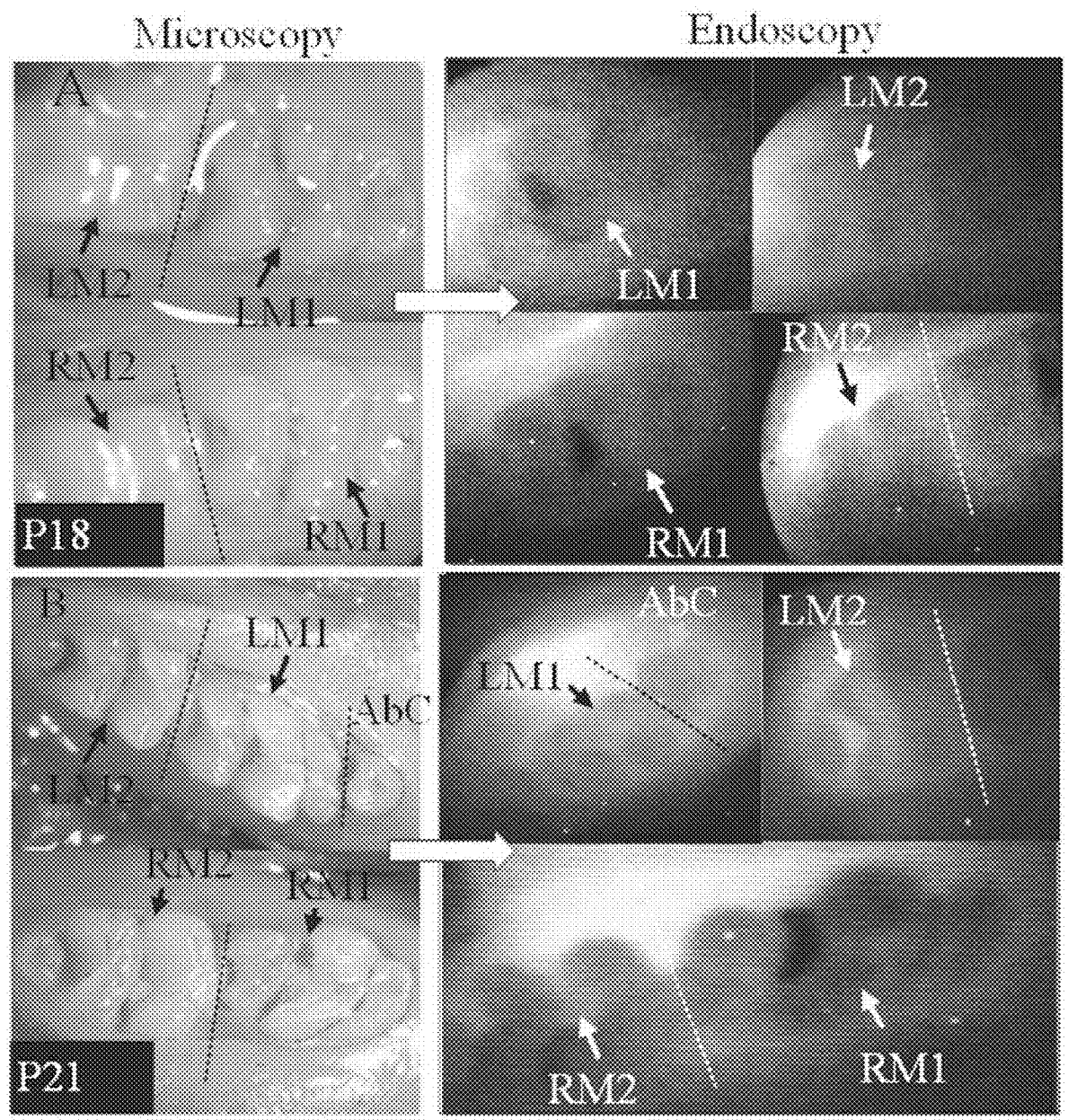
FIG. 4 shows microscopic bright-field and endoscopic NIR fluorescence tooth images for the erupted molars of P18 and P21 rats after 24 hours of injection. (A) The microscopic bright-field photographs and endoscopic fluorescence images of P18 rat. (B) The microscopic bright-field photographs and endoscopic fluorescence images of P21 rat. AbC: abnormal cusp. Excitation: 785 nm LD.

After the molar eruption, the cusp features of the rat molars become much clearer than before, as shown in bright-field photographs (FIG. 4, panels A and B). From the endoscopic fluorescence images in FIG. 4, panels A and B, the profiles of the first and second molars on P18 and P21 rats become easily distinguished, and each cusp of both the first and second molars also can be observed. Due to the flat structures of the buccal and lingual cusps of the P18 rat, the profiles of the molars are not as clear as that of the P21 rat (FIG. 4, panel A). Overall, most of the information about the morphology of the molars of the P21 rat is clearly observed from the endoscopic fluorescence images, including the buccal and lingual cusps (FIG. 4, panel B).

In addition, abnormal dental structures were detected with the NIR fluorescence dental imaging system. Tooth abnormalities, including the agenesis of the third molars (wisdom teeth), irregular tooth size, shape, and structure, affect ~20% of the human population.[32] Various factors can affect tooth development resulting in abnormality of molar cusps. In one of the P21 rats examined, a small abnormal cusp occurring in the left first molar (LM1) as compared to the right first molar (RM1) was observed with a microscope (FIG. 4, panel B).

The Optimal Imaging Condition

Figure 5:
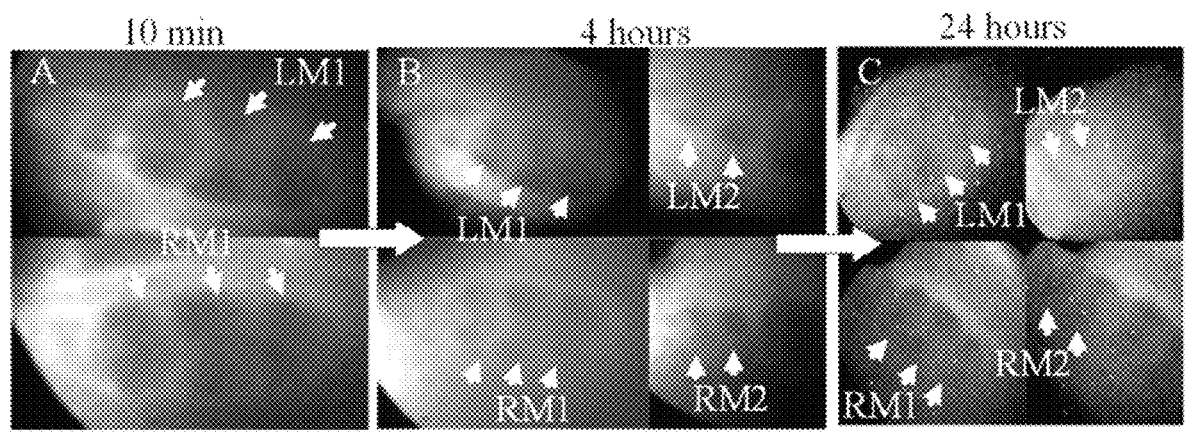
FIG. 5 shows endoscopic fluorescence images for P14 rats with different injection time. (A)-(C) The endoscopic fluorescence images of P14 rats after injection of 10 minutes, 4 hours, and 24 hours, respectively. LM: left molar; RM: right molar; LM1 and LM2: left molars 1 and 2, RM1 and RM2: right molars 1 and 2. Excitation: 785 nm LD.

To determine the influence of the imaging windows (from the moment of ICG injection to the moment of observation) and the contributions of the near-infrared light on NIR fluorescence dental imaging, three P14 rats were injected with ICG dye and sacrificed 10 minutes, 4 hours and 24 hours after injection. After only 10 minutes of injection, all three cusps of the first molar can be observed clearly from the endoscopic fluorescence images (FIG. 5, panel A). When extending the imaging window to 4 hours, the profiles of the cusps of the first molar become a bit clearer than those of the rat with 10 minutes of injection, and two cusps of the second left and right molars can be observed from the endoscopic fluorescence images. But the detailed structures of the cusps of the first molars are still a bit blurred (FIG. 5, panel B). With longer injection periods (24 hours), two cusps of the second molars become recognizable, and more detailed information on the morphology of the buccal and lingual cusps of the first and second molars can be obtained from the endoscopic fluorescence images (FIG. 5, panel C).

Figure 6:
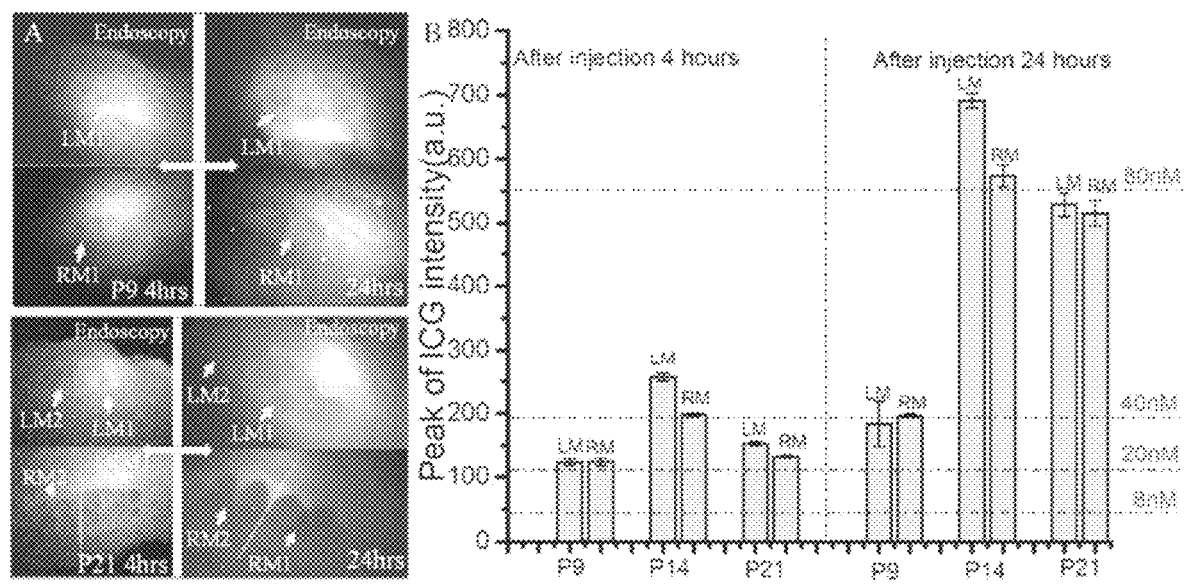
FIG. 6 shows imaging windows for P9 and P21 rat tooth imaging and ICG concentration in the dental tissues. (A) The endoscopic fluorescence images of P9 and P21 rats after 4 and 24 hours of injection. (B) The peak intensities of the ICG spectra around the left and right molar at 4 hours and 24 hours after ICG injection. The blue lines in (B) show the fluorescence intensity for the gradients of ICG concentration, diluted into 4% BSA/PBS solutions. Excitation: 785 nm LD.

Although a clear profile of P14 molar can be obtained in as little as 10 minutes after ICG injection, the imaging window of 24 hours can facilitate acquisition of more efficient NIR tooth images. To explore and optimize the interaction of postnatal age and imaging window, P9 and P21 rats were sacrificed and imaged 4 hours after the injection. The cusps of these two rats are blurred and unrecognizable, and are not as distinguishable as those of rats having a 24-hour imaging window (FIG. 6, panel A). Therefore, based on these results, 24 hours appears to be an optimized imaging window for the variously postnatal rats.

Meanwhile, to study ICG distributions in the dental tissues, ICG intensity was collected from the dental tissues of two P9 rats, two P14 rats, and two P21 rats, and the rats with each postnatal period were sacrificed 4 hours and 24 hours after injection, respectively. From FIG. 6, panel B, the trend of the ICG intensity at the 4-hours imaging window is similar to that at the 24-hours imaging window. P14 rats have the largest peak of ICG intensity, followed by P21 and P9 rats. As for the fluorescence intensities at the two imaging windows, the fluorescence at the 24-hour imaging window almost doubled, compared to that at the 4-hour window (FIG. 6, panel B). From the gradients of ICG intensity (the dot-dash lines in FIG. 6, panel B), ICG concentrations in dental tissues range from 20 nM to 200 nM for the P9, P14 and P21 rats with 4 and 24 hour imaging windows. Overall, ICG concentration in the dental tissues increased with the injection time but fluctuated among the different postnatal periods.

Although the incisor of mice and rats are teeth of continuous eruption, their molars are teeth of limited eruption, similar to human.[33] Thus, rats and mice are often used as animal models in dental research. For example, rat first molars are usually used in studying odontogenesis and relevant findings have been successfully extrapolated to human odontogenesis research.[34] Accordingly, the systems and techniques disclosed herein can be applied to imaging of human teeth, as well as other bodily tissues. A recent publication reported to develop novel root canal treatments using rats as model animals.[35] Here it is reported that postnatal rat pups were injected with ICG dye, and dental imaging was successfully acquired with endoscopy under NIR condition. This demonstrates for the first time that NIR fluorescence method can be used for dental imaging. The results provide evidence for the development of NIR fluorescence (ICG)-based dental imaging system in human dentistry. This confirms that the endoscopic NIR imaging can be a useful tool to monitor tooth development and eruption. The endoscope in combination with NIR camera can generate significantly more useful information about the morphology of the teeth than traditional bright-field imaging with visible (VIS) light.

The data provided herein indicate that the development stage of the teeth has a great effect on the quality (resolution) of the NIR imaging. For the molars of P9 rats under the VIS condition, the endoscope was not able to obtain high-resolution and clear bright-field tooth images. However, the condition could be greatly improved by the NIR method. In this imaging range, light has lower absorption by blood, water, and lipids;[28-30] therefore, the signal-to-noise ratio in imaging is greatly enhanced, while the autofluorescence is minimized.[28-30] The tissue penetration of light can be as good as 1-2 cm,[28-31] which can help to image the dental tissues underneath the surface (FIG. 3).[10] As the pups become older at the period of P14, P18, and P21, endoscopic fluorescence images become clearer to show the profiles of the first and second molars, and even the buccal and lingual cusps can be recognized. Particularly, the buccal and lingual cusps and other detailed morphology of P21 rats can be obtained from the endoscopic fluorescence images. The main factor is that the enamel of the first and second molars become more mineralized and less transparent than that of P9 rats.[36, 37] Based on the observation provided herein, it can be reasoned that tooth mineralization and fluorescence wavelength are critical factors for resolution of NIR endoscopic imaging.

Conventional dental imaging methods usually rely on X-ray radiograph, and the experimental rats have to be sacrificed at a particular time point, and only discontinuous and stationary results can be obtained for dental images with X-ray methods.[9] It is well-known that X-ray, as an ionizing radiation method, can bring in harmful and potentially lethal impacts: ~2% of the invasive cancer incidence is directly related to the X-ray based medical imaging radiation exposure.[38-42] Such impacts are of greater concerns for children than adults as they are required to take 3~6 times more frequent dental X-rays, because of their rapid growth and decay of teeth.[38-42] There is no safe dose threshold "below which the risk of tumor induction is zero," as concluded by US National Academy of Sciences Biological Effects of Ionizing Radiation Committee.[43] The dental imaging systems and methods described herein are based on NIR emission (650-950 nm), which does not involve any ionizing radiation risk to the patients, a major advantage compared to the prevalent dental X-ray imaging.

Meanwhile, the period from P1 to P10 is crucial for the development of tooth germ.[44] At this stage, the molars have minimal mineralization and still are in the dental follicle, and typically histological method is employed to explore the mechanism of the molar development. But it suffers from complicated specimen preparations and operations, and insufficient 3D dental imaging.[45] Hence, there is a shortage of a cost-efficient, and easy-to-use method that can continuously monitor the molar development or movement, and development of ionizing-radiation-free and easy-to-use method is greatly in demand.

To meet that demand, an endoscopic NIR fluorescence dental imaging system is disclosed herein to image rat molars at different developmental stages. The results show that the detailed information about the morphology of the unerupted and erupted molars can be obtained as early as postnatal 9 days that cannot be detected under the visible condition, and even an abnormally shaped cusp can be clearly observed. Also, the systems and methods described herein can be used to continuously monitor the molars intraoperatively at the early development stage in vivo. This technique is an ionizing-radiation-free method that may potentially apply for human dental imaging. Also, this imaging method may be valuable for a real-time monitoring for image-guided dental surgeries.

In human NIR imaging, the imaging window varies from, for example, only several seconds or minutes for head and neck cancer imaging by the intravenous administration,[16] to over 3 hours for lymph node detection by local intradermal injection, and days to weeks for cancer imaging.[46] According to the existing studies on ICG-based human imaging, ICG is not involved into any known metabolites and is quickly extracted by the liver.[13, 15] In the methods disclosed herein, ICG was administrated by the intradermal injection from the backside so as to avoid fast clearance. The results indicate that NIR dental imaging can realize as short as 10 minutes for the P14 rats, but 24-hours seems to be an optimal imaging window for new-born rats with different postnatal periods (FIG. 6).

The variations of ICG spectra between left and right sides of mandibles in some rats were also observed (FIG. 6). These may be caused by the chewing-side preference of the individual pups or may be due to the injection points closer to left or right side.

FIG. 7 shows a schematic diagram of the dental imaging system 700 according to some embodiments, integrated into an endoscope 702 through its biopsy channel 704. The system 700 includes a spectroscopic device 706 (See FIG. 8) including a device probe 708 that is introduced into the biopsy channel 704 of the endoscope 702. According to some embodiments, the device probe 708 includes a bifurcated optical fiber, such as the fiber shown in FIG. 8. The system 700 also includes an NIR camera 710 optically coupled to a second lumen 712 of the endoscope 702. The system 700 may also include a data processor in communication with the spectroscopic device 706 and the NIR camera 710 (See FIG. 23). The system 700 can be used to obtain endoscopic NIR images of dental structures in vivo. The system 700 may also include a white light source and white light camera 714. White light can be transmitted through additional lumens 716, 718 of the endoscope 702.

FIG. 8 shows the design of optical paths in the spectroscopic device system according to some embodiments. The optical paths may be included in a flexible device probe, and/or a bifurcated fiber, for example. A first channel (e.g., the upper channel) delivers the excitation light from the light source to the samples to be imaged. The light source may be a near-infrared illumination source. According to some embodiments, the first channel provides the excitation light for both the NIR camera and the spectroscopic imaging. A second channel (e.g., the lower channel) delivers the fluorescence from the sample back to the spectrometer for spectroscopic imaging. According to some embodiments, the system includes additional light sources. For example, the NIR camera may include an additional light source, or the system may include an additional light source that is not included in the NIR camera.

The systems and methods disclosed herein may be used to identify critical tooth structures that may not be observed by the traditional bright-field imaging. This may be due to the much deeper tissue penetration depth by NIR light than by VIS light. The time post-ICG administration and the ages of the tooth are two important factors affecting the imaging. The endoscopic NIR fluorescence imaging can be a useful alternative tool to X-ray based imaging for diagnosis and surgeries in dental clinics. This imaging method has unique advantages of providing an ionizing-radiation-free and easy-to-use approach that can continuously monitor the tooth development in real-time.

REFERENCES

1. Gonzales, C., H. Hotokezaka, Y. Arai, et al. 2009. An in vivo 3D micro-CT evaluation of tooth movement after the application of different force magnitudes in rat molar. The Angle orthodontist. 79: 703-714.
2. Hsieh, Y.-S., Y.-C. Ho, S.-Y. Lee, et al. 2013. Dental optical coherence tomography. Sensors. 13: 8928-8949.
3. Kattainen, H., J. Tuukkanen, U. Simanainen, et al. 2001. In utero/lactational 2,3,7,8-tetrachlorodibenzo-p-dioxin exposure impairs molar tooth development in rats. Toxicol Appl Pharmacol. 174: 216-224.
4. Nakajima, A., M. Murata, E. Tanaka, et al. 2007. Development of three-dimensional FE modeling system from the limited cone beam CT images for orthodontic tipping tooth movement. Dent Mater J. 26: 882-891.
5. Schambach, S. J., S. Bag, L. Schilling, et al. 2010. Application of micro-CT in small animal imaging. Methods. 50: 2-13.
6. Holdsworth, D. W. & M. M. Thornton. 2002. Micro-CT in small animal and specimen imaging. Trends In Biotechnology. 20: S34-S39.
7. Badea, C., M. Drangova, D. Holdsworth, et al. 2008. In vivo small-animal imaging using micro-CT and digital subtraction angiography. Physics in medicine and biology. 53: R319.
8. Kosaka, N., M. Mitsunaga, M. R. Longmire, et al. 2011. Near infrared fluorescence-guided real-time endoscopic detection of peritoneal ovarian cancer nodules using intravenously injected indocyanine green. International journal of cancer. 129: 1671-1677.
9. Xu, X., J. Zhou, F. Yang, et al. 2016. Using Micro-Computed Tomography to Evaluate the Dynamics of Orthodontically Induced Root Resorption Repair in a Rat Model. PLoS One. 11: e0150135.
10. Alander, J. T., I. Kaartinen, A. Laakso, et al. 2012. A review of indocyanine green fluorescent imaging in surgery. International journal of biomedical imaging. 2012: 940585.
11. Parthasarathy, A. B., S. H. Chong, F. A. Moscatelli, et al. 2015. "Intraoperative imaging of tumors with indo-cyanine green fluorescence with an endoscope". In SPIE BiOS: 93110X-93110X-93116. International Society for Optics and Photonics.
12. AV, D. S., H. Lin, E. R. Henderson, et al. 2016. Review of fluorescence guided surgery systems: identification of key performance capabilities beyond indocyanine green imaging. Journal of biomedical optics. 21: 80901.
13. Schmidt, F., A. Dittberner, S. Koscielny, et al. 2017. Feasibility of real-time near-infrared indocyanine green fluorescence endoscopy for the evaluation of mucosal head and neck lesions. Head Neck. 39: 234-240.
14. Maarek, J. M., D. P. Holschneider, J. Harimoto, et al. 2004. Measurement of cardiac output with indocyanine green transcutaneous fluorescence dilution technique. Anesthesiology. 100: 1476-1483.
15. Schaafsma, B. E., J. S. Mieog, M. Hutteman, et al. 2011. The clinical use of indocyanine green as a near-infrared fluorescent contrast agent for image-guided oncologic surgery. J Surg Oncol. 104: 323-332.
16. Yokoyama, J., M. Fujimaki, S. Ohba, et al. 2013. A feasibility study of NIR fluorescent image-guided surgery in head and neck cancer based on the assessment of optimum surgical time as revealed through dynamic imaging. Onco Targets Ther. 6: 325-330.
17. Yokoyama, J., K. Ishibashi, H. Shiramizu, et al. 2016. Impact of Endoscopic Indocyanine Green Fluorescence Imaging on Superselective Intra-arterial Chemotherapy for Recurrent Cancer of the Skull Base. Anticancer Res. 36: 3419-3424.
18. Plante, M., O. Touhami, X. B. Trinh, et al. 2015. Sentinel node mapping with indocyanine green and endoscopic near-infrared fluorescence imaging in endometrial cancer. A pilot study and review of the literature. Gynecol Oncol. 137: 443-447.
19. Huang, Z., Z. Huang, D. Zhang, et al. 2016. Endoscopically-assisted operations in the treatment of odontogenic peripheral osteomyelitis of the posterior mandible. The British journal of oral & maxillofacial surgery. 54: 542-546.
20. Shah, N., N. Bansal & A. Logani. 2014. Recent advances in imaging technologies in dentistry. World journal of radiology. 6: 794.
21. Vandenberghe, B., R. Jacobs & H. Bosmans. 2010. Modern dental imaging: a review of the current technology and clinical applications in dental practice. Eur. Radiol. 20: 2637-2655.
22. Cox, B. & P. Beard. 2015. Imaging techniques: Super-resolution ultrasound. Nature. 527: 451-452.
23. Marotti, J., S. Heger, J. Tinschert, et al. 2013. Recent advances of ultrasound imaging in dentistry—a review of the literature. Oral surgery, oral medicine, oral pathology and oral radiology. 115: 819-832.
24. Fujimoto, J. G. 2003. Optical coherence tomography for ultrahigh resolution in vivo imaging. Nature biotechnology. 21: 1361.
25. Wojtkowski, M., V. Srinivasan, J. G. Fujimoto, et al. 2005. Three-dimensional retinal imaging with high-speed ultrahigh-resolution optical coherence tomography. Ophthalmology. 112: 1734-1746.
26. Lungova, V., R. J. Radlanski, A. S. Tucker, et al. 2011. Tooth-bone morphogenesis during postnatal stages of mouse first molar development. J Anat. 218: 699-716.
27. Abdelwahab, M., A. M. A. Elfattah, Y. W. Khafagy, et al. 2017. Endoscopic enucleation of large jaw cysts: Promising outcomes. Auris Nasus Larynx.
28. Smith, A. M., M. C. Mancini & S. Nie. 2009. Bioimaging: second window for in vivo imaging. Nat. Nanotechnol. 4: 710-711.
29. Weissleder, R. 2001. A clearer vision for in vivo imaging. Nat. Biotechnol. 19: 316-316.
30. Frangioni, J. V. 2003. In vivo near-infrared fluorescence imaging. Curr. Opin. Chem. Biol. 7: 626-634.
31. Mohs, A. M., M. C. Mancini, S. Singhal, et al. 2010. Hand-held spectroscopic device for in vivo and intraoperative tumor detection: contrast enhancement, detection sensitivity, and tissue penetration. Anal. Chem. 9058-9065.
32. Fleischmannova, J., E. Matalova, A. S. Tucker, et al. 2008. Mouse models of tooth abnormalities. Eur. J. Oral Sci. 116: 1-10.
33. Wise, G. & W. Fan. 1989. Changes in the tartrate-resistant acid phosphatase cell population in dental follicles and bony crypts of rat molars during tooth eruption. Journal of dental research. 68: 150-156.

34. Fleischmannova, J., E. Matalova, A. S. Tucker, et al. 2008. Mouse models of tooth abnormalities. Eur J Oral Sci. 116: 1-10.
35. Yoneda, N., Y. Noiri, S. Matsui, et al. 2017. Development of a root canal treatment model in the rat. Sci Rep. 7: 3315.
36. Baler, C. M., P. Ngaotheppitak & D. Fried. 2005. Imaging of occlusal dental caries (decay) with near-IR light at 1310-nm. Optics Express. 13: 573-582.
37. Lyngstadaas, S. P., C. B. Moinichen & S. Risnes. 1998. Crown morphology, enamel distribution, and enamel structure in mouse molars. Anat Rec. 250: 268-280.
38. Anand, P., A. B. Kunnumakara, C. Sundaram, et al. 2008. Cancer is a preventable disease that requires major lifestyle changes. Pharm. Res. 25: 2097-2116.
39. Lin, E. C. 2010. "Radiation risk from medical imaging". In Mayo Clin. Proc., Vol. 85: 1142-1146. Elsevier.
40. de González, A. B., M. Mahesh, K.-P. Kim, et al. 2009. Projected cancer risks from computed tomographic scans performed in the United States in 2007. Arch. Intern. Med. 169: 2071-2077.
41. Brenner, D. J. & E. J. Hall. 2007. Computed tomography—an increasing source of radiation exposure. N. Engl. J. Med. 357: 2277-2284.
42. Association, A. D. 2012. Dental radiographic examinations: recommendations for patient selection and limiting radiation exposure. Chicago: ADA.
43. Council, N. R. 2006. Health risks from exposure to low levels of ionizing radiation: BEIR VII phase 2. National Academies Press.
44. Taniguchi, K., K. Okamura, M. Hayashi, et al. 1999. The effect of mechanical trauma on the tooth germ of rat molars at various developmental stages: a histopathological study. Endod Dent Traumatol. 15: 17-25.
45. Gonzales, C., H. Hotokezaka, Y. Arai, et al. 2009. An in vivo 3D micro-CT evaluation of tooth movement after the application of different force magnitudes in rat molar. Angle Orthod. 79: 703-714.
46. Fujiwara, M., T. Mizukami, A. Suzuki, et al. 2009. Sentinel lymph node detection in skin cancer patients using real-time fluorescence navigation with indocyanine green: preliminary experience. Journal of Plastic, Reconstructive & Aesthetic Surgery. 62: e373-e378.

EXAMPLES

The following describes some concepts of the current invention with reference to particular embodiments. The general concepts of the current invention are not limited to the examples described.

It was estimated that over 25% of the human population suffered from impacted teeth (delayed or failed eruption); the highest incidence occurs on the third molar.[1,2] X-ray imaging is the most common diagnostic tool for clinical examination of patients with impacted teeth.[3-5] Particularly, computed tomography (CT) is used in three-dimensional (3D) visualization of tooth structures.[3-5] To date, there is a great need for patients to take routinely dental imaging. Dental radiography occupies almost one-third of total radiological examinations in western countries;[6] for example, American Dental Association (ADA) recommends that dental imaging should be taken at least once every 1~3 years.[7] However, the greatest disadvantage of X-ray imaging is the ionizing radiation exposure (X rays causes ionizing effects on human tissues), which may lead to killing or malfunctioning of cells at high doses[8] X-ray radiation exposure may also be attributable to ~2% of invasive cancer incidents.[9,10] In dentistry, X-ray radiation risks are of higher concern to children, who on average have to take X-ray radiation 3-6 times more frequently than adults, due to their rapid rates of teeth growth and decay.[7,8,10]

There are a few non-ionizing-radiation dental imaging methods in development, Magnetic Resonance Imaging (MRI) is considered to be safe for 3D dental imaging without ionizing radiation risk.[3] However, due to its high cost, its use in dentistry is limited to assess precise diagnostics for exceptional cases.[3,11] Ultrasound (US) imaging is another non-invasive, inexpensive and painless method;[3] however, this method has limitations in detecting the periodontal ligament and in diagnosing fractures.[3,12] Additionally, optical coherence tomography (OCT) becomes popular in dental research—because of its safety, noninvasive imaging, and excellent spatial resolution (~20 μm).[13] Nonetheless, it is limited to a restricted scanning range due to low penetration depth.[13] Therefore, it will be of great significance to develop an efficient and easy-to-use dental imaging technique for intraoperative diagnosis in dental surgeries without ionizing radiation risk.

Near-infrared (NIR) imaging, especially fluorescence imaging, plays an essential role in many areas of biomedical sciences.[14,15] In dentistry, existing research focuses on using NIR light, with a wavelength of 1310 nm, to acquire high imaging contrast between the caries lesions and sound teeth.[16,17] Few studies reported using NIR light with the enhancement of indocyanine green (ICG) to image dental tissues of impacted teeth.[18] ICG, approved by Food and Drug Administration (FDA) for clinical uses,[19] is known to produce NIR fluorescence (650-950 nm) in angiography.[14,20] Currently, ICG is widely used in retinal angiography, cancer surgical imaging, and lymph-node detection.[19,21,22] ICG was reported to serve as a photosensitizer dye or a photo-absorbing dye for dental treatments.[23,24]

Meanwhile, use of the endoscope under NIR condition could provide significant information regarding tumors (e.g., feeding artery) as compared to wide-field imaging.[19] When used in dentistry, the endoscope not only helps to significantly reduce the patient pain, but also helps them to recover from dental surgery.[25] To our best knowledge, ICG-enhanced endoscopic dental imaging has not been systematically investigated.[18,26] Described herein is the feasibility of this approach to generate in vivo NIR dental images of the developing molars of postnatal rats and the potential factors that can be optimized to improve the imaging quality.

In Vivo NIR Dental Imaging of Unerupted Molars

Figure 9:
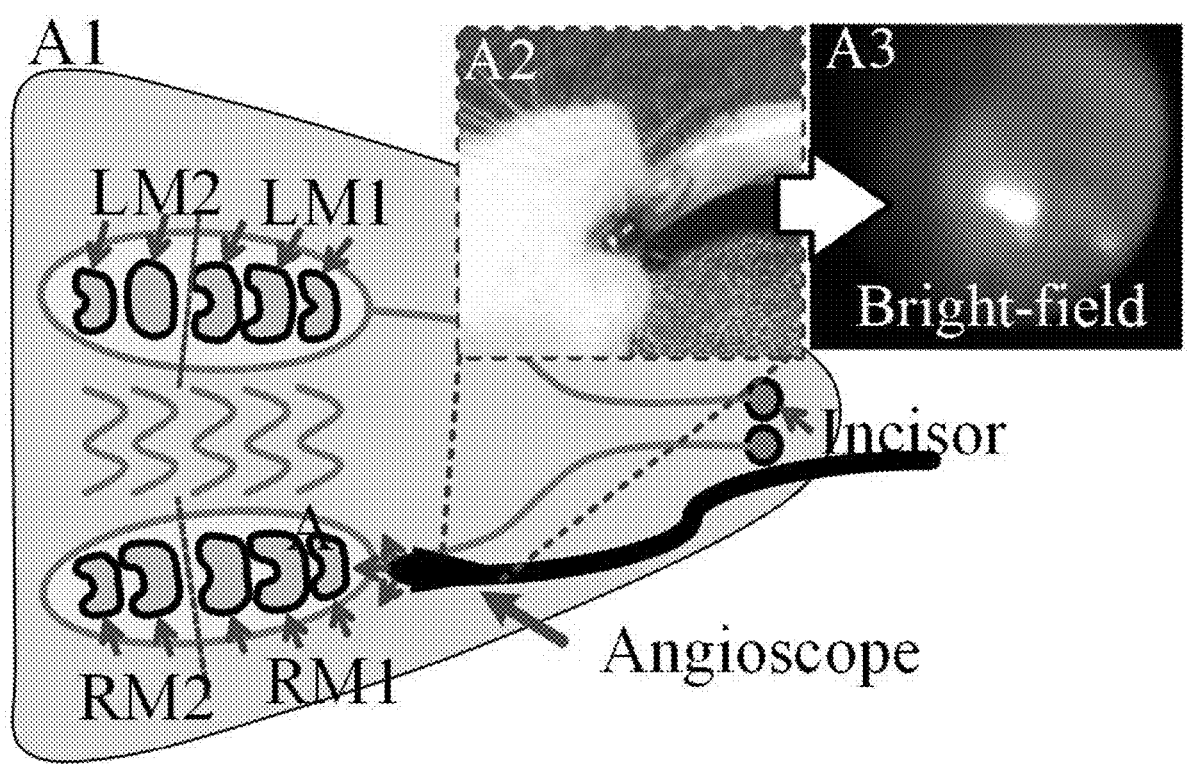
FIG. 9 shows a schematic diagram of the rat oral cavity and angioscope (A1), and bright-field photographs of the unerupted molar observed by angioscope (A2, A3).
Figure 10:
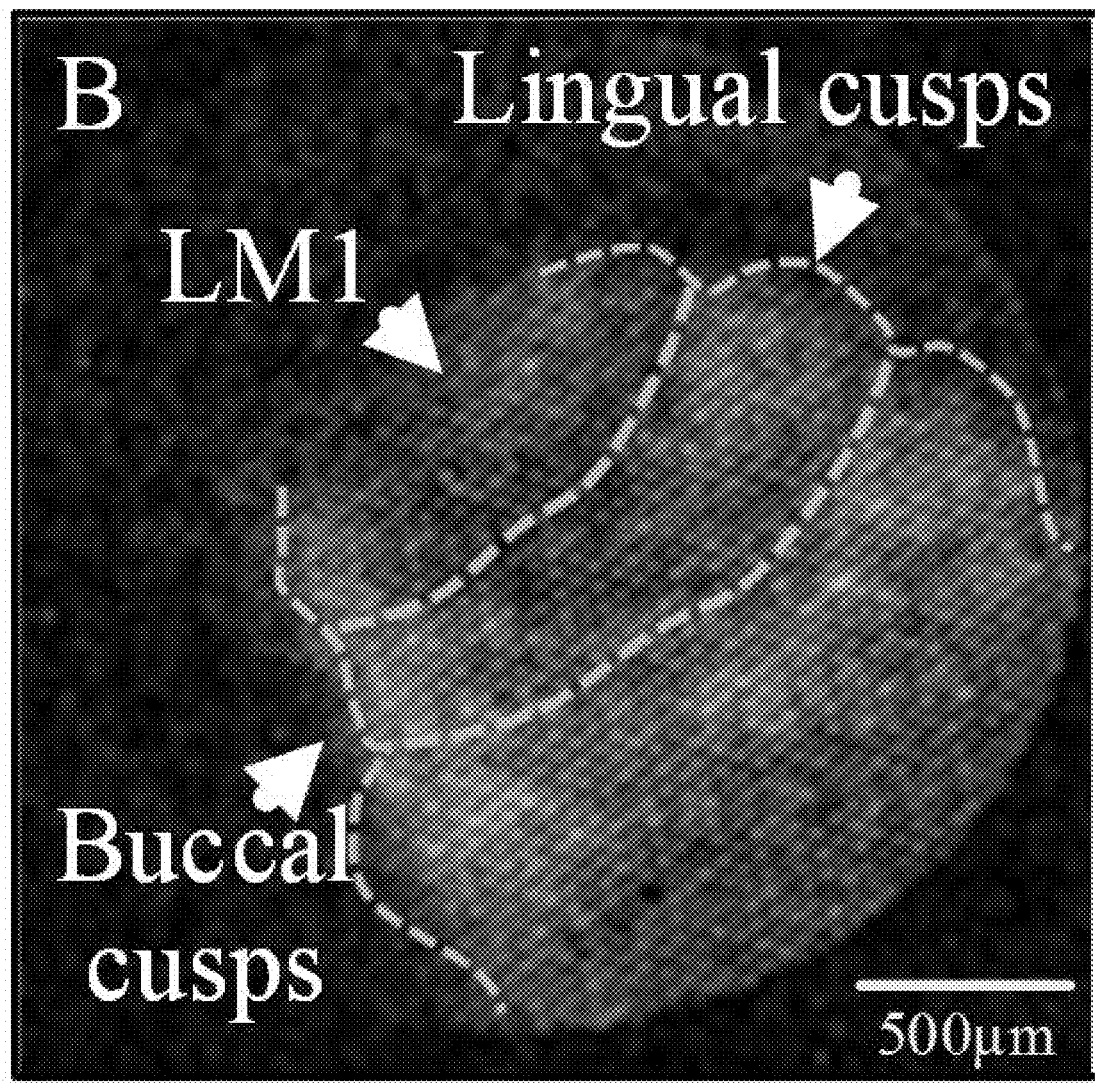
FIG. 10 shows an NIR fluorescence image of the P14 molars, taken by camera with the angioscope.
Figure 11:
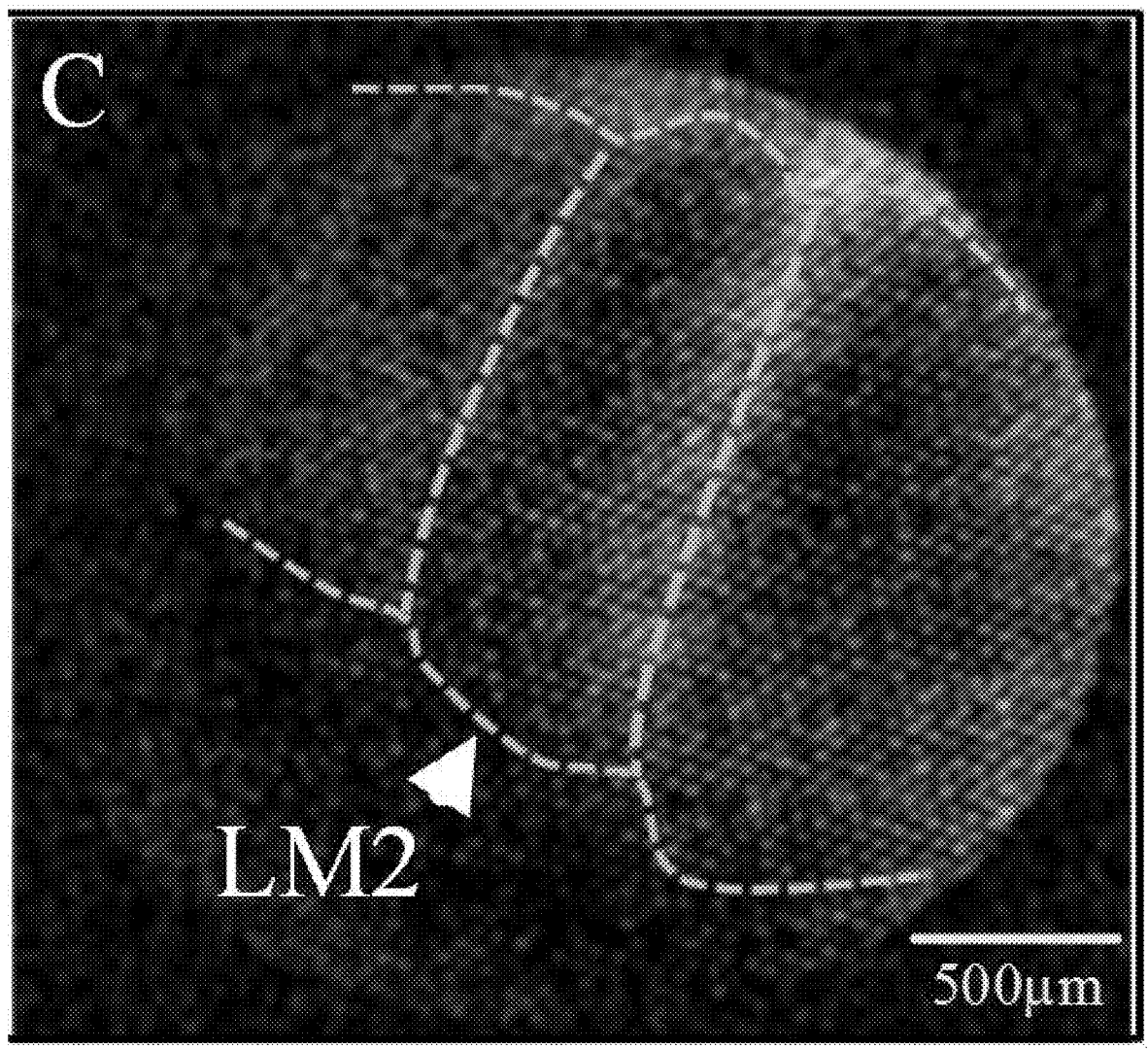
FIG. 11 shows another NIR fluorescence image of the P14 molars, taken by camera with the angioscope.

FIGS. 9-11 show in vivo dental imaging of uninterrupted molars. In the in vivo dental imaging, one P14 rat was imaged after 72 hrs of ICG intradermal injection via the intradermal method. The deflecting tip (front end) of the angioscope was inserted into the rat oral cavity and was moved forward and backward to detect the molars in situ (FIG. 9, panels A1-A3). In FIG. 9, panel A1 is a schematic diagram of the rat oral cavity and angioscope, and panels A2 and A3 are bright-field photographs of the unerupted molar observed by angioscope. Under visible conditions (bright-field), only a bright reflection spot was seen and no molar structure profiles were obtained from the bright-field imaging identified (FIG. 9, panel A2).

FIGS. 10 and 11 show NIR fluorescence images of the P14 molars, taken by camera with the angioscope. With our ICG-assisted NIR imaging system described herein, through the angioscope, clear morphological profiles of the molars were observed in situ from the angioscopic fluorescent images, and even the cusps (raised points on the crowns of teeth) were unambiguously distinguished (FIG. 10). By adjusting the imaging angle of the deflecting tip, more detailed morphology of the molars (such as buccal and lingual cusps) was identified from the fluorescence images (FIG. 11).

Ex Vivo NIR Dental Imaging of Unerupted Molars

Figure 12:
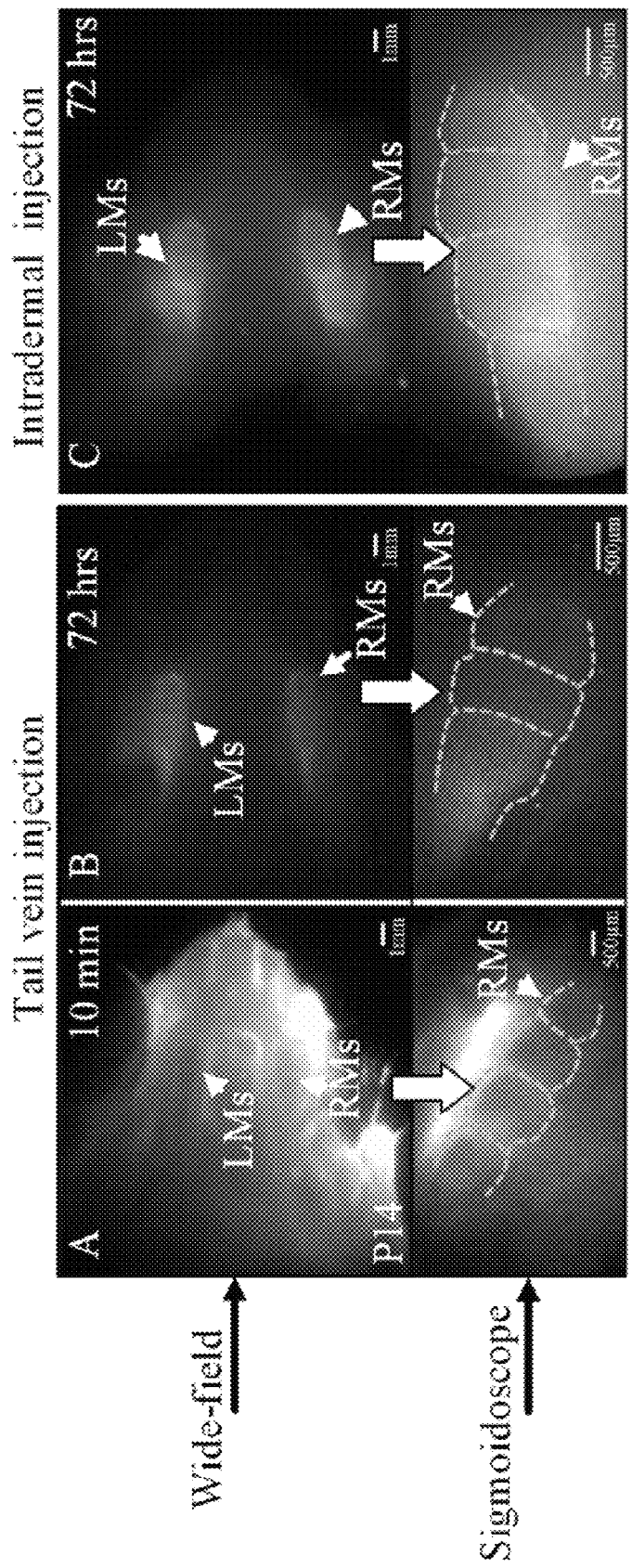
FIG. 12 shows Ex vivo NIR dental imaging for the unerupted molars from P14 rats. (A): 10-min imaging window; (B) and (C): 72-hr imaging window. (A) and (B): tail vein injection of ICG; (C): intradermal injection of ICG; the same P14 rat as in the in vivo imaging (FIG. 1). LMs: left molars; RMs: right molars. Molar sketch: the dashed lines.

FIG. 12 shows ex vivo NIR dental imaging for the unerupted molars from P14 rats. To obtain the ex vivo NIR dental images, one P14 rat was imaged at 10 min after injection (panel A). Two other P14 rats, including the P14 rat in the previous in vivo study, were imaged by the NIR imaging system after 72 hrs of injection (panels B and C). All three P14 molars were imaged under the wild-field and the sigmoidoscopic conditions.

In the wide-field imaging, dental structures of the P14 rat (panel A) at the 10-min imaging window (from the moment of ICG injection to the moment of observation) showed brighter fluorescence than that of the two P14 rats at the 72-hr imaging window (panels B and C).

The entire mandibular area was bright at 10-min after injection. In contrast, when the imaging window was prolonged to 72 hrs, only molar regions remained prominent for both injection methods (FIG. 12, panels B and C), which facilitated the observation of dental structures.

In the endoscopic NIR imaging (FIG. 12, panels B and C), the molar profiles of the P14 rats could be distinguished easily at 72 hrs after injection; the 10-min imaging window achieved even better imaging contrast; each cusp was recognized clearly from the endoscopic images (FIG. 12, panel A).

The Impact of Injection Methods on NIR Dental Imaging

Two P9 rats were used to investigate the effect of different injection methods on NIR dental imaging. Specifically, one of the P9 rats was administered 10 μL (~0.5 mg/kg bodyweight) ICG via the tail vein injection, while the other was injected by the intradermal injection. Both rats were imaged by NIR camera with the endoscope under visible and NIR conditions at 24 hrs.

Figure 13:
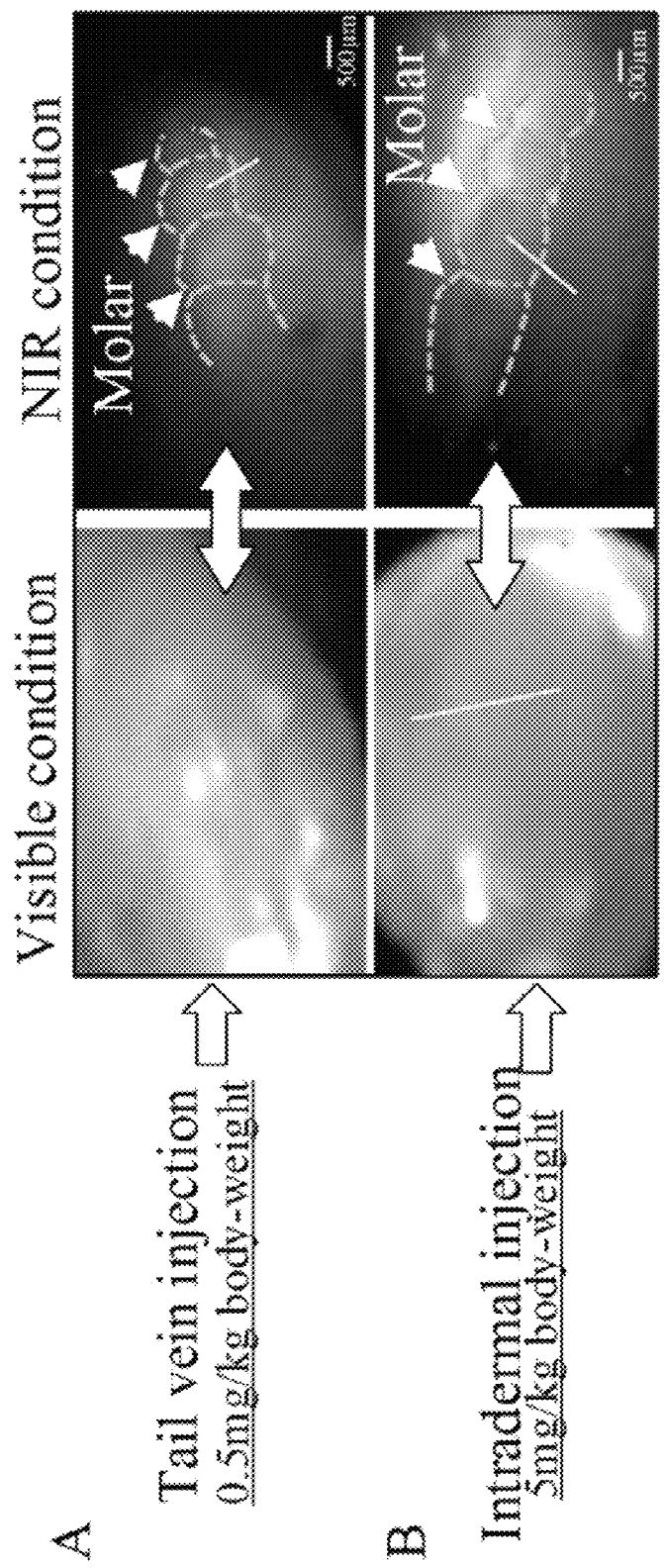
FIG. 13 shows NIR dental imaging (bright-field imaging vs. NIR imaging) for P9 rats with (A) tail vein injection and (B) intradermal injection. Molar sketch: the dashed lines.
Figure 14:
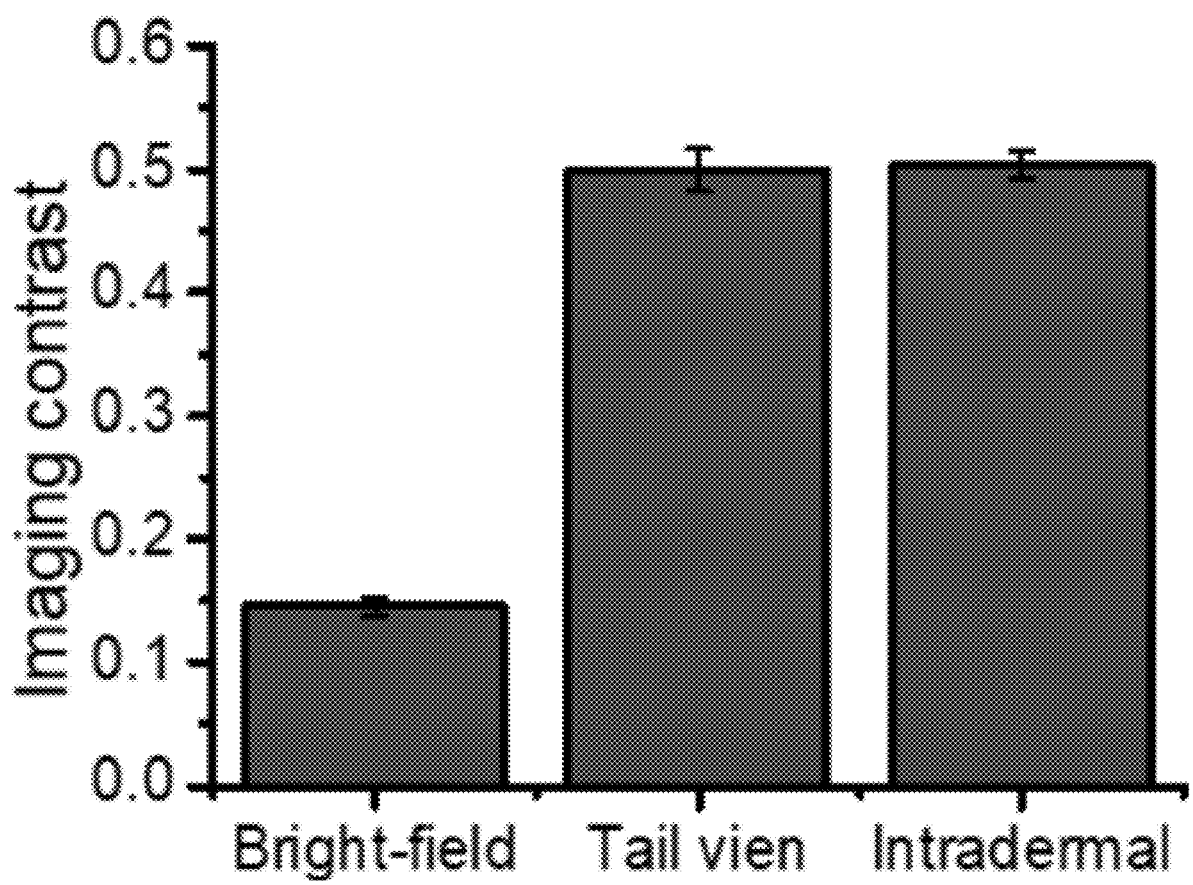
FIG. 14 shows the grayscale difference imaging contrast between the molar regions and surrounding tissues. The pixels are sampled from the solid lines in FIG. 13.

Under the visible condition, the profiles of the molars were unable to be distinguished from the surrounding tissues (left images in FIG. 13, panels A and B). However, under NIR condition, three cusps of the first molar were clearly recognized from the endoscopic fluorescence images (right images in FIG. 13, panels A and B). From the quantitative analysis of grayscale difference, the bright-field imaging contrast was much lower than that of the NIR imaging, but the two injection methods did not show obvious effect on image quality (FIG. 14).

The Impact of Intraoral and Extraoral Excitations on NIR Dental Imaging

Two P14 rats with the tail vein injection were imaged at 24-hr and 96-hr imaging windows under either intraoral or extraoral light excitation conditions. When at the 24 hr imaging window (FIG. 15, panels A and B), the profiles of P14 molars with the intraoral excitation showed better imaging contrast than that of the extraoral excitation.

Figure 15:
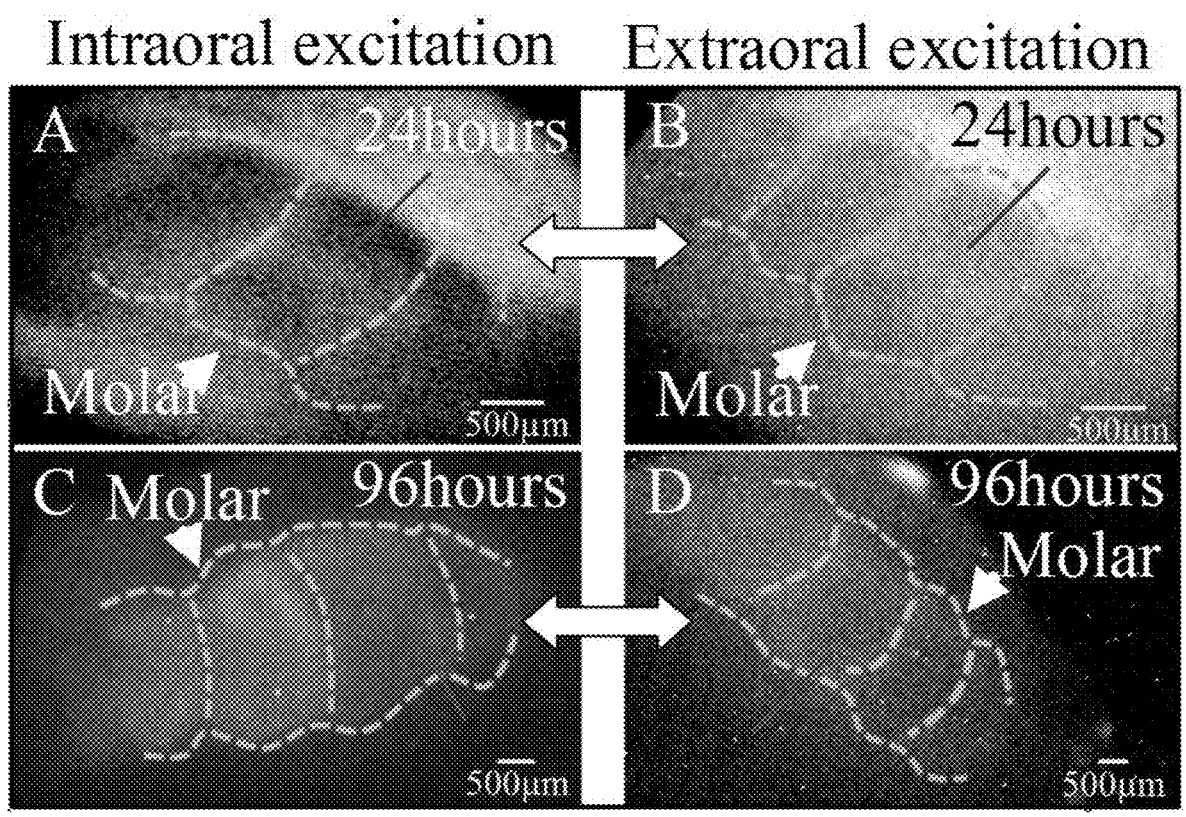
FIG. 15 shows NIR dental imaging of the P14 rats with the intraoral and extraoral excitation; ICG was administered into the rats by the tail vein injection. The rats were sacrificed and imaged at 24 hrs ((A), (B)) or 96 hrs ((C), (D)): after injection. Molar sketch: the dashed lines.
Figure 16:
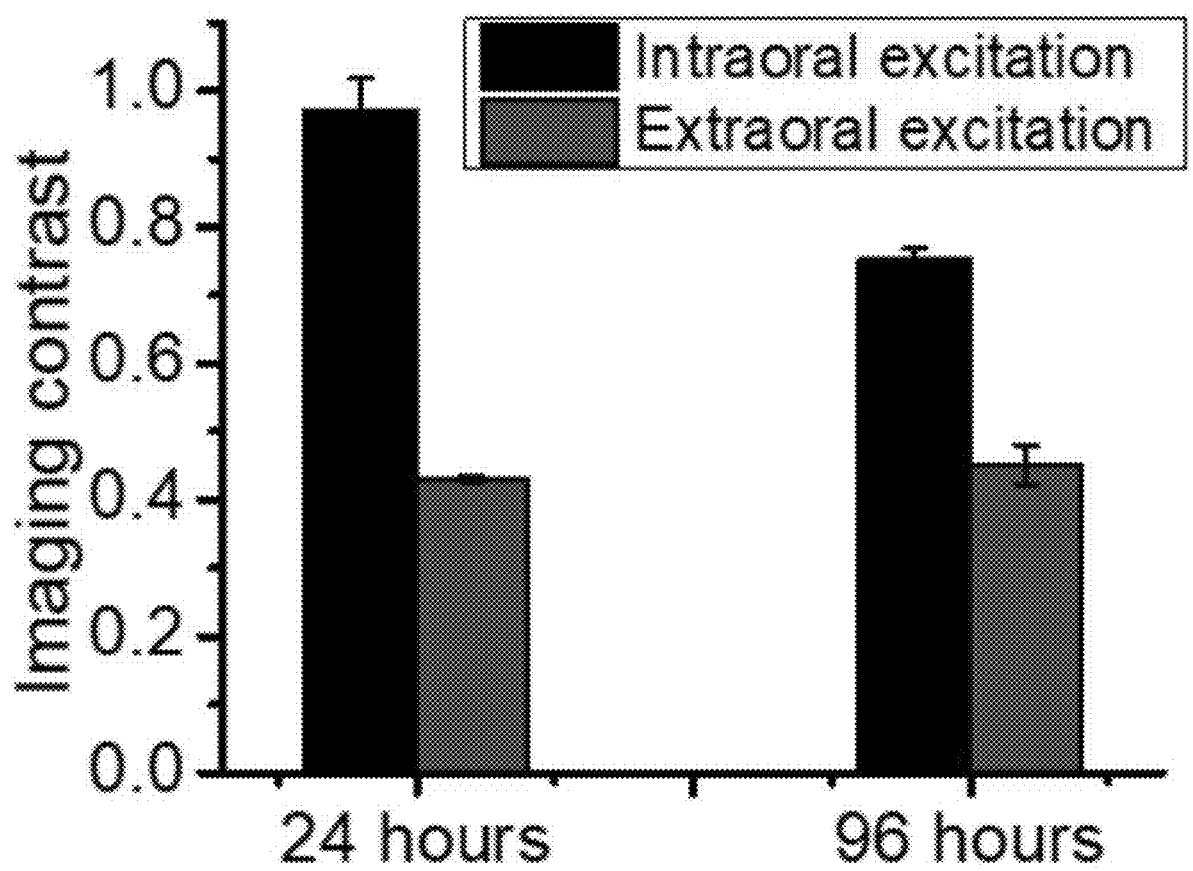
FIG. 16 shows a quantitative analysis on imaging contrast: the normalized grayscale difference between the molar regions and surrounding tissues, based on the data sampled from the solid lines in FIG. 15.

When the imaging window was prolonged to 96 hrs, only the molar regions remained prominent (FIG. 15, panels C and D). This facilitated the identification of molar structures, however, it should be noted that the image contrast slightly decreased at 96 hrs as compared to 24 hrs (FIG. 15, panels C and D vs. panels A and B). For the grayscale difference, the intraoral excitation had a larger magnitude than that of the extraoral excitation for both imaging windows; the 24-hr imaging window had a larger difference than the 96-hrs imaging window (FIG. 16).

Figure 17:
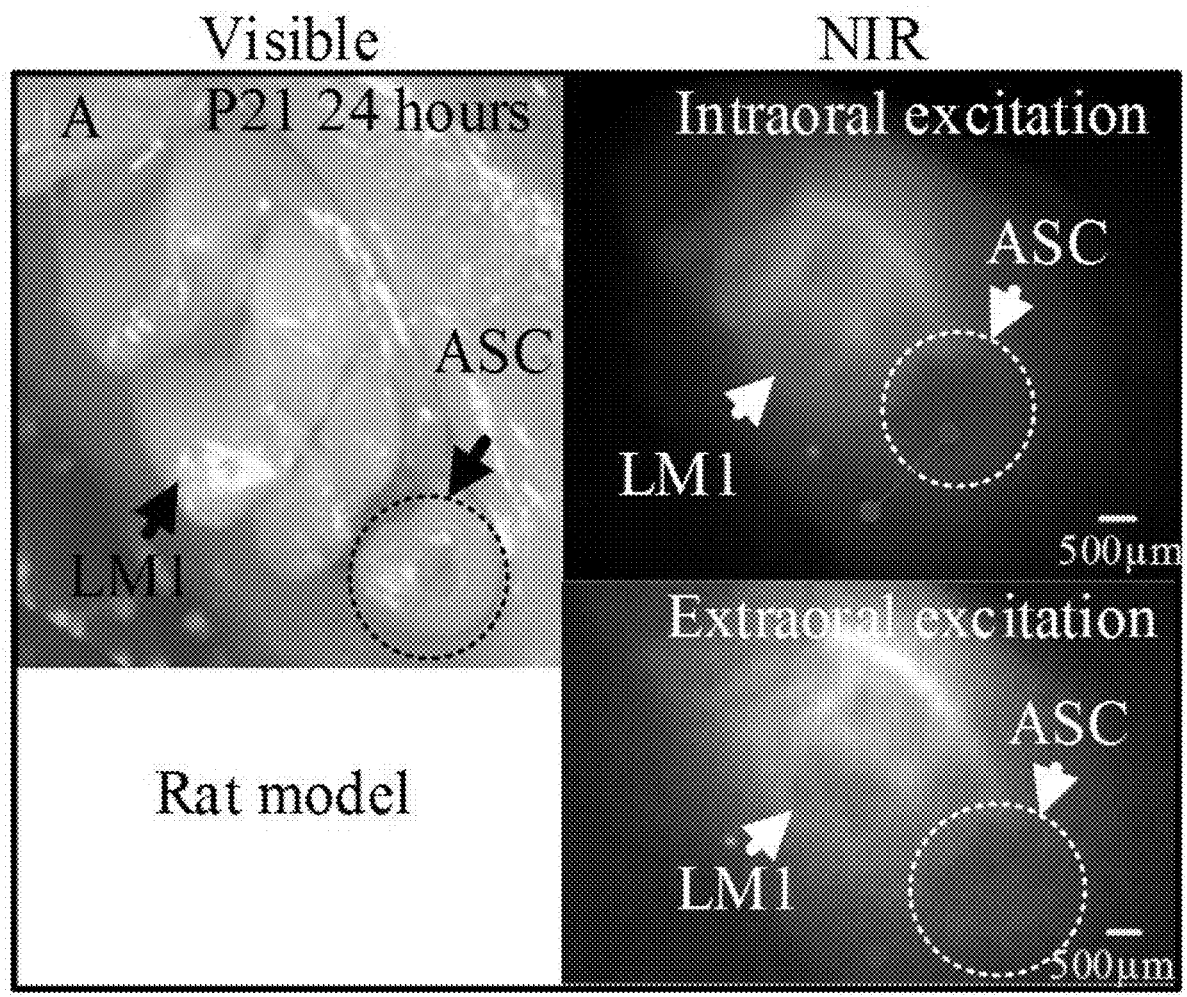
FIG. 17 shows NIR dental imaging of the erupted molars of a P21 rat, as well as human tooth; the rat was administered by the intradermal injection and imaged at the 24-hr window; the human tooth was immersed into ICG solution for 24 hours. Bright-field images taken by microscopy are on the left, and the intraoral and extraoral excitation are on the right. LM1: left first molar; ASC: Abnormally shaped cusp.
Figure 18:
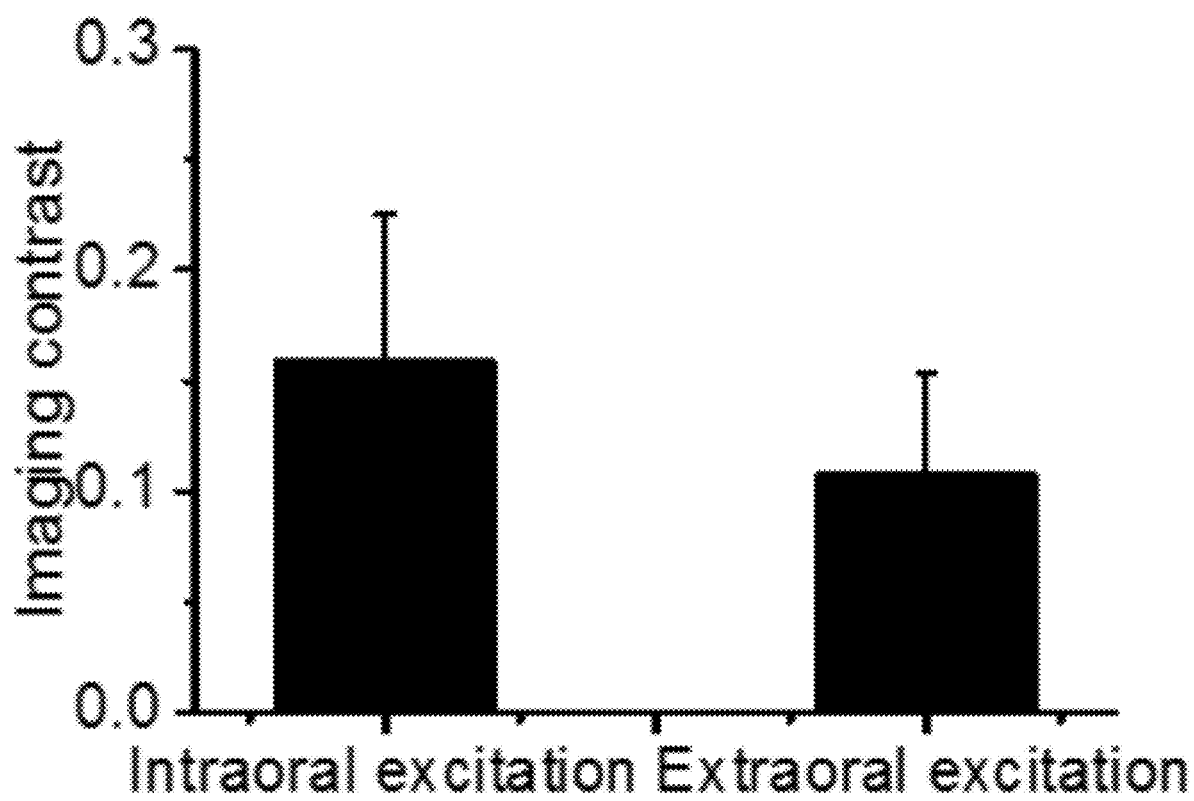
FIG. 18 shows a quantitative analysis of imaging contrast between the molar regions and surrounding tissues, based on the data sampled from the solid lines in the NIR images in FIG. 17.

In one of the P21 rats, an abnormally shaped cusp (ASC) was found in the left first molar (LM1) (FIG. 17). To explore the impact of two ICG excitation methods on detecting abnormal molars, this P21 rat was imaged at the 24-hr window. Under NIR condition (FIG. 17), the abnormal cusp could be clearly recognized by both the two excitation methods; the intraoral excitation demonstrated better imaging contrast to distinguish the abnormal cusp and the sound molar than that of the extraoral excitation. The grayscale difference also demonstrated quantitatively that the intraoral excitation had a better imaging contrast that did the extraoral excitation (FIG. 18).

Figure 19:
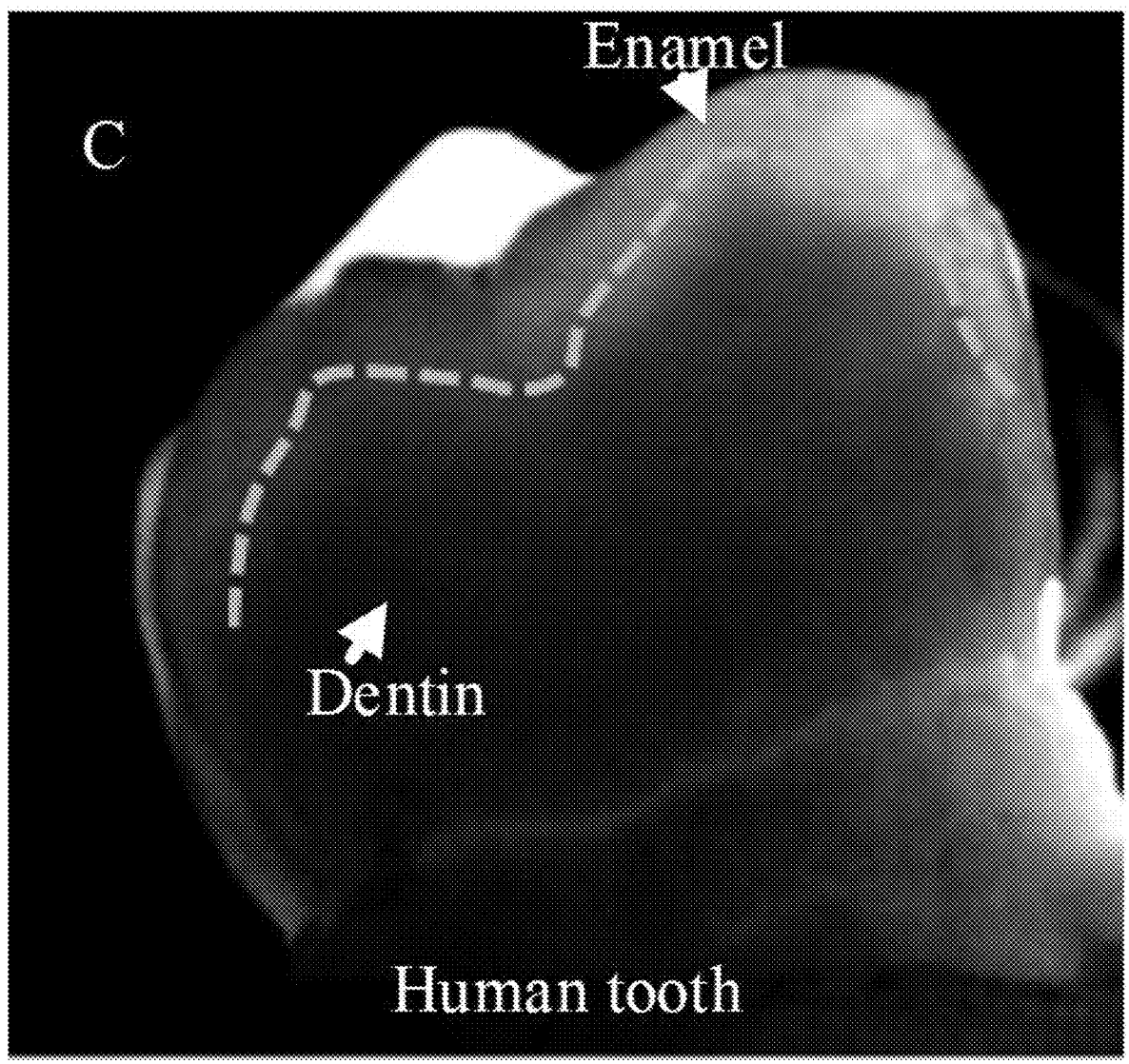
FIG. 19 shows a sound human tooth under ICG-assisted NIR dental imaging. Boundary of enamel and dentin: the dashed line.

In addition, a sound human tooth was immersed into 1 μM ICG solution for 24 hours to show the feasibility of ICG-assisted NIR dental imaging for human dentistry. From ICG-assisted dental image, the morphology of human tooth was able to be observed clearly; the enamel become transparent, while the dentin is relatively darker; the profiles of dentin were clearly delineated (FIG. 19).

NIRF Dental Imaging for Detecting Human Superficial Caries

Figure 20:
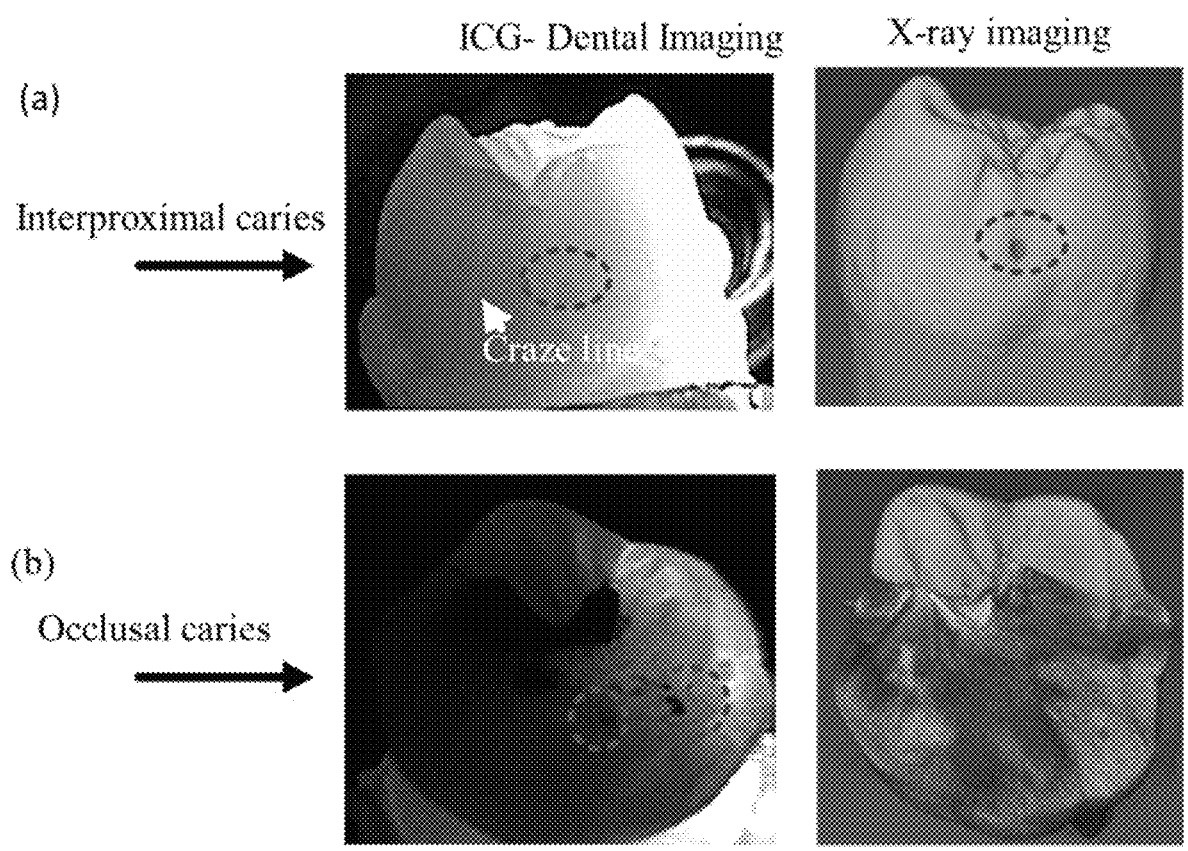
FIG. 20 shows ICG dental imaging for superficial caries and compared to 3D X-ray imaging. (a) Comparison of the superficial interproximal caries of the same tooth under ICG dental imaging, and 3D X-ray imaging; (b) The superficial occlusal caries under ICG dental imaging, and 3D X-ray imaging.

One interproximal superficial caries and two occlusal superficial caries were found in two different teeth (FIG. 20). The interproximal caries was recognized as a dark dot from ICG dental image; a craze line near the interproximal caries was clearly detected from the ICG-NIRF-I image (FIG. 20, panel A). The interproximal caries was also recognized from the 3D X-ray image. However, the craze line near caries failed to be detected by microCT. Compared to interproximal caries, two occlusal caries were shown as dark dots and could be recognized easily from the surrounding enamels in ICG imaging method; but none of occlusal caries could be detected from the 3D X-ray image (FIG. 20, panel B).

Spectral Analysis in NIR Dental Imaging

Figure 21:
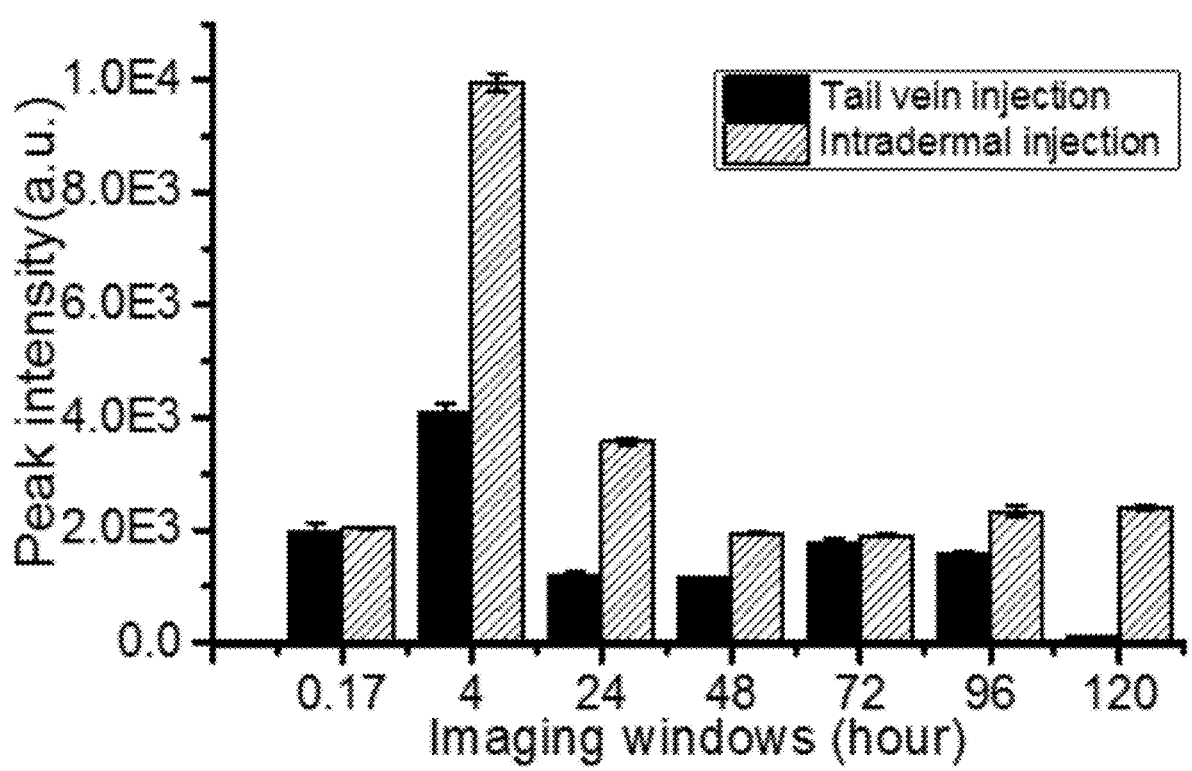
FIG. 21 shows the peak intensity of ICG spectra of P14 rats in the dental tissues for two injection methods at various imaging windows: 10 minutes (0.17 hr), 4 hrs, 24 hrs, 48 hrs, 72 hrs, 96 hrs, and 120 hrs.
Figure 22:
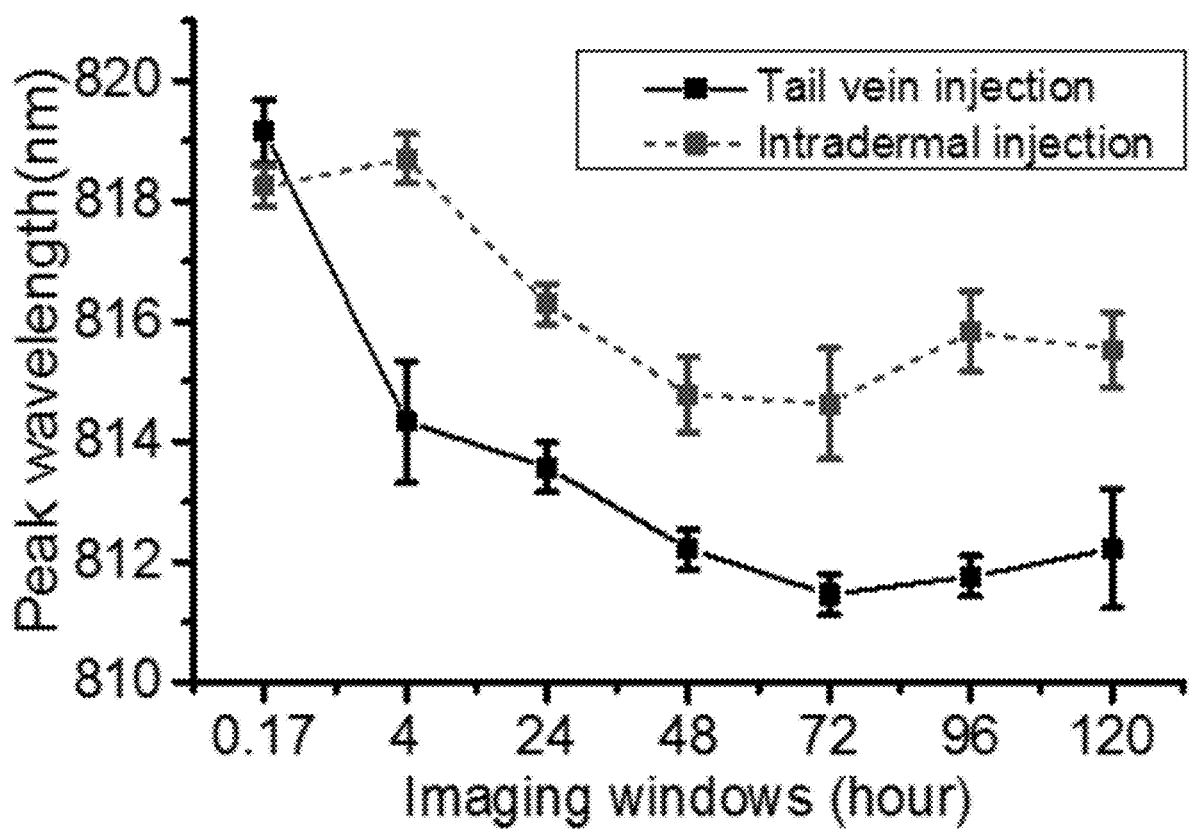
FIG. 22 shows the peak wavelength of ICG spectra of P14 rats in the dental tissues for two injection methods at various imaging windows: 10 minutes (0.17 hr), 4 hrs, 24 hrs, 48 hrs, 72 hrs, 96 hrs, and 120 hrs. The corresponding peak wavelength shifts with the imaging windows.

FIGS. 21 and 22 show characteristics of ICG spectra in NIR dental imaging. Regarding the peak intensity, ICG fluorescence reached the maximum at 4 hrs after injection (FIG. 21). ICG accumulation in the molar tissues by the intradermal injection was larger than that by the tail vein injection. After 24-hrs of injection, both injection methods had a significant decrease of ICG intensity with the imaging window. Thereafter, the magnitude kept relatively stable for both injection methods until 96 hrs after ICG injection. Finally, ICG intensity became nearly zero at 120-hr after the tail vein injection, while this value remained significant for the intradermal injection.

As for the peak wavelength shifts (FIG. 22), both injection methods had the same peak wavelength (~819 nm) at the beginning, but there was ~3 nm difference after 24 hrs of injection. At 4 hrs after injection, the peak wavelength by the intradermal injection still remained ~819 nm, while the peak wavelength by the tail vein injection dropped to ~814 nm. After that, there was a slight blue-shift of ICG peak wavelength over time for both injection methods. Eventually, the peak wavelength stayed at 815 nm for the intradermal injection and 812 nm for the tail vein injection.

The first molars of rat are one of the most common animal models in studying odontogenesis, because of its similarity in limited eruption like humans.[27] Many findings and results obtained from rat molars have been applied successfully in human dental research and diagnosis.[28] As disclosed herein, postnatal rats were injected with ICG agents; the NIR dental imaging system (camera+spectroscopic device), in conjunction with the endoscopes, was designed to observe, in vivo and ex vivo, the dental structures of postnatal rats after ICG administration. The results of this animal study showed that ionizing-radiation-free ICG-enhanced NIR dental imaging can be used to image dental structures of unerupted molars.

This imaging technique has the potential for diagnosis of tooth eruption disorders and other dental abnormalities.

Imaging structures of unerupted molars is impossible by regular bright-field imaging since the molars are buried underneath the tissues;[29] observation of the morphology of an anomalously unerupted tooth is an integral part of diagnosis and treatment planning.[29] ICG-based NIR dental imaging can acquire clear tooth images for the unerupted molars in as short as 10 min after ICG injection (FIG. 12, panel A). Within a 24-hr imaging window, the brightness of the surrounding tissues was relatively stronger than that of the unerupted molars (FIG. 12, panel A).

At the prolonged imaging windows (72 hrs), only the molar area remained prominent in P14 rats (FIG. 12, panels B and C). This could be due to the trapping of ICG agents in dental tissues because of the abrupt cessation in cell proliferation at later stages of tooth development.[30] A major advantage of this phenomenon is the in vivo dental imaging with the angioscope. This method can readily locate the molars and therefore reduce the time necessary for the procedure. The angioscopic in situ tooth images provide clear details on the morphology of the molars.

As seen in the ex vivo dental images of P9 rats, NIR improved the imaging quality significantly and helped to observe molar structures that were not recognized under visible conditions (FIGS. 13 and 14). This indicates that the imaging system in the NIR range (800-950 nm) has a good tissue penetration depth likely due to the fact that NIR light in this range (650-950 nm) has lower absorption by blood, water, and lipids.[31,32] As a result, the signal-to-noise ratio in the imaging can be greatly enhanced, while the autofluorescence is minimized.[31,32] Therefore, ICG-based dental imaging is more convenient to use for imaging unerupted and impacted teeth, when compared to 1310 nm NIR light that is reported for dental imaging.[16,17]

Meanwhile, the results also demonstrated that both extraoral and intraoral ICG-excitation methods were able to observe unerupted molars and abnormally shaped cusp of erupted molars. The capability of clearly imaging dental tissues with intraoral illumination was a result of the good tissue penetration by the NIR range (800-950 nm) used in some embodiments of the invention.[31,32] Additionally, the intraoral illumination is more likely to gather more fluorescence photons to generate clearer dental images. Although the current prevalent X-ray imaging and CT also have good tissue penetration, X-ray based dental imaging methods have several drawbacks, including radiation risks to the patients, complicated and expensive equipment and incapable real-time imaging.[3-6] The data disclosed herein suggests that ICG-enhanced NIR dental imaging can be used as a safe (ionizing radiation-free), portable and real-time imaging system for diagnosis and surgeries in dental clinics.

In human ICG-based imaging, low-dosage ICG agent is usually administered by intravenous injection and is transported by the blood circulation.[19,33] For lymph-node imaging, ICG with the intradermal injection is transported via the lymphatic circulation.[34] As disclosed herein, it was found that both the injection methods and the imaging windows were effective on features of ICG spectra (wavelength shifts). From the observation of peak intensity changing over time, the intravenous injection had faster excretion rate than that of the intradermal injection (at 120 hrs of injection) (FIG. 21). Also, the tail vein injection with lower dosage has the similar imaging contrast and quality when compared to the intradermal injection with high dosage (FIG. 21).

ICG agents are known to bind to plasma proteins through the intravenous injection, causing a wavelength shift of up to 25 nm, when compared to ICG in the water (805 nm).[35] The shift in the fluorescence wavelength may be attributed to the microenvironment changes surrounding ICG, which indicates the dynamic association of dyes and tissues.

When caries reach the dentin at the dentin-enamel junction, decay quickly spreads laterally.[37] Early detection of caries provides a chance for effective conservative dental care in the form of decay removal and restoration and opens the possibility of re-mineralization if diagnosed in early stages.[38] For the data disclosed herein, FDA-approved NIR exogenous fluorophore, the ICG, was used to significantly improve the image contrast. ICG dental imaging acquired clear images of the interproximal and occlusal superficial caries. Under NIR conditions, superficial caries were observed as dark dots under the NIR light. Particularly, ICG dental imaging clearly imaged even small caries lesions of occlusal caries, which was failed to be detected by the dental X-ray; in the 3D X-ray images, the small caries lesions were overlapped by the micro-CT defections caused by the metallic amalgam filling (FIG. 20). ICG NIR imaging method proved to be a radiation-free, non-invasive diagnostic tool for the detection of caries.

According to some embodiments of the invention, the NIR dental imaging system, in combination with the endoscope, can provide more valuable information on dental morphology than that of wide-field imaging. For the optimized imaging conditions, imaging quality can be improved for in vivo dental imaging at 72 hrs after ICG injection; intraoral illumination has better imaging contrast than the extraoral illumination; the two injection methods almost have no effect on imaging quality. Due to the small dimension (1-2 mm) of rat molars, the imaging was relatively noisy in the rat dental imaging, but was improved significantly in human tooth (cm in dimension) imaging. ICG-assisted NIR dental imaging can also image human tooth efficiently and obtain the clear profile of the tooth (FIG. 19). With ICG-aided contrast, the enamel became transparent in NIR I window (800-950 nm), while the dentin was easily distinguished from the enamel (FIG. 19). NIRF dental imaging has its unique features for the diagnosis of caries. The imaging resolution of this method is as good as 100 μm, much better than dental ultrasound.[3] ICG-enhanced NIR dental imaging has the potential to become a safe and real-time in vivo imaging tool in dental diagnosis and treatment (surgeries), especially for tooth eruption disorders.

Endoscopic NIR Dental Imaging System

Figure 23:
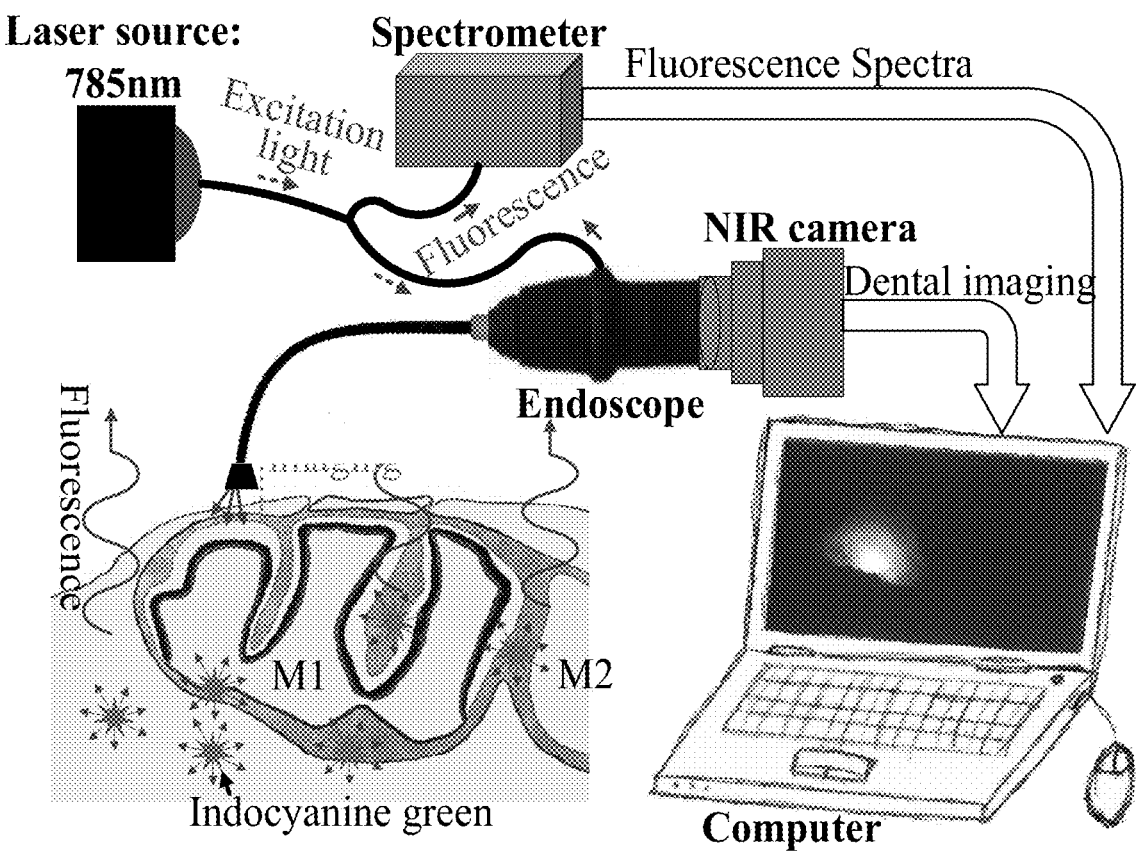
FIG. 23 shows the NIR dental imaging according to some embodiments of the invention. M1: first molar, M2: second molar.

The system according to some embodiments is a miniaturized NIR dental imaging system (spectroscopic device+ camera) that is suitable for in situ rapid fluorescence imaging in dentistry. The system consists of a laser light source (for example, a 785 nm laser diode, Turnkey Raman Lasers-785 Series; Ocean Optics, Inc), a spectrometer (for example, QEPro; Ocean Optics, Inc), an imaging module, and a computer. A schematic diagram of the system is shown in FIG. 23.

According to some embodiments, the laser light source delivers light (for example, 785 nm light) to excite ICG, while the spectrometer records the spectrum of ICG fluorescence. The imaging module includes an NIR camera (for example, Guppy F038B; Allied Vision Technologies GmbH), in conjunction with an angioscope (for example, Olympus, PF Type 22) for in vivo dental imaging, and a sigmoidoscope (for example, Olympus, OSF-3) for ex vivo dental imaging. Two filters (for example, bandpass lens: 785 nm, long pass lens: 800 nm; Thorlabs Inc) are used to optimize the detection of ICG spectrum from 800 to 950 nm; a custom-designed bifurcated fiber transmits the excitation and emission fluorescence.

Reagents and Animals

For the data disclosed herein, ICG powder, bovine serum albumin (BSA, 96%), and phosphate buffered saline (PBS) were purchased from Sigma-Aldrich (St. Louis, MO). Ultra-pure water (18.2 MΩ) was used to prepare the reagents throughout this study. For injection, ICG powder was dissolved in ultrapure water with the maximum solubility (1 mg/mL). For the preparation of the standard ICG spectra, the ICG solution was diluted to concentrations ranging from 2 nM to 80 μM (2 nM for each gradient) with 4% BSA-PBS.

Sprague Dawley rats with different postnatal ages were used. A total of eleven P14 (Postnatal 14 days) rats were used for the in vivo and ex vivo imaging to optimize imaging conditions and study the features of ICG spectrum. Two P9 rats were used to study the effects of the injection methods on the dental imaging, while one P21 rat was used for imaging abnormally shaped molars.

The experimental rats were administered ICG solution by two methods: 1) intradermal injection (from the backside) with 5 mg/kg body-weight; 2) tail vein injection with 10 μL, dose per rat (0.3-0.5 mg/kg).

Acquiring Rat Dental Images

The NIR camera, in conjunction with the sigmoidoscope, was used for the ex vivo dental imaging, in which the deflecting tip of the sigmoidoscope was fixed at ~4 mm above the rat molar samples. For in vivo dental imaging, the deflecting tip of the angioscope with the NIR camera was inserted into the rat's oral cavity to acquire molar images.

For the extraoral ICG excitation, the laser fiber head was fixed at about 5 mm below the specimens to excite ICG agents, while the deflecting tip of the endoscope was above the molar of interest. For the intraoral ICG excitation, the laser fiber was inserted into the working channel of the sigmoidoscope; the deflecting tip imaged the dental structures from the top of the specimens.

To explore spectral properties (such as intensity and peak wavelength) of ICG fluorescence under various NIR dental imaging conditions quantitatively (e.g. imaging windows and injection methods), ICG spectra was tested on the dental tissues in P14 rats by two distinct injection methods. The spectra of dental tissues in P14 rats were recorded from 10 min to 120 hrs after ICG injection.

Imaging Contrast-Normalized Grayscale Difference

To quantitatively analyze the imaging contrast (the difference between two regions of interest), two groups of 10 pixels in the rat dental images were respectively sampled from the molars and surrounding tissues by a designated line. Each group of the pixels was selected from the crests or troughs of the grayscale curve of the designated line. The grayscale of each certain pixel corresponds to the ICG fluorescence intensity recorded at that pixel by the camera. A parameter was defined as $G_{diff}$, which represents the imaging contrast between the molars and surrounding tissues.

To calculate $G_{diff}$, the selected pixels were sorted first by equation (1) from the minimum grayscale to the maximum grayscale; then $G_{diff}$ was calculated by equation (2):

$$\text{sort}(g) = (g_{min}, \ldots, g_{max}) \quad (1)$$

$$G_{diff} = \text{avg}(\Sigma_{i=0}^{9} |\text{sort}(g_m)_i - \text{sort}(g_s)_i|) / \text{avg}(\Sigma_{i=0}^{9} g_m + \Sigma_{i=0}^{9} g_s) \quad (2)$$

where $g_m$ and $g_s$ are the grayscales of the pixels from the molars and the surrounding tissues.

REFERENCES—EXAMPLES

1. Sener., I., Turer., A., Bereket., C. & Ozdemir., M. Non-Syndromic Familial Unerupted Teeth_A Rare Contidion. Cumhuriyet Dental Journal 18, 359-363, doi:10.7126/cdj.58140.1008002068 (2013).
2. Pereira, I. F., Santiago, F. Z. M., Sette-Dias, A. C. & Noronha, V. Taking advantage of an unerupted third molar: a case report. Dental Press J Orthod 22, 97-101, doi:10.1590/2177-6709.22.4.097-101.oar (2017).
3. Shah, N., Bansal, N. & Logani, A. Recent advances in imaging technologies in dentistry. World J Radiol 6, 794-807, doi:10.4329/wjr.v6.i10.794 (2014).
4. Kiljunen, T., Kaasalainen, T., Suomalainen, A. & Kortesniemi, M. Dental cone beam CT: A review. Phys Med 31, 844-860, doi:10.1016/j.ejmp.2015.09.004 (2015).
5. Hsieh, Y. S. et al. Dental optical coherence tomography. Sensors (Basel) 13, 8928-8949, doi:10.3390/s130708928 (2013).
6. Metsala, E., Henner, A. & Ekholm, M. Quality assurance in digital dental imaging: a systematic review. Acta Odontol Scand 72, 362-371, doi:10.3109/00016357.2013.840746 (2014).
7. Association, A. D. Dental radiographic examinations: recommendations for patient selection and limiting radiation exposure. Chicago: ADA (2012).
8. Valentin, J. The 2007 recommendations of the international commission on radiological protection. (Elsevier Oxford, 2007).
9. Lin, E. C. in Mayo Clin. Proc. 1142-1146 (Elsevier).
10. de González, A. B. et al. Projected cancer risks from computed tomographic scans performed in the United States in 2007. Arch. Intern. Med. 169, 2071-2077 (2009).
11. Bolouri, C. et al. Performance of orthopantomography, planar scintigraphy, CT alone and SPECT/CT in patients with suspected osteomyelitis of the jaw. European journal of nuclear medicine and molecular imaging 40, 411-417 (2013).
12. Adeyemo, W. & Akadiri, O. A systematic review of the diagnostic role of ultrasonography in maxillofacial fractures. International journal of oral and maxillofacial surgery 40, 655-661 (2011).
13. Hsieh, Y.-S. et al. Dental optical coherence tomography. Sensors 13, 8928-8949 (2013).
14. Alander, J. T. et al. A review of indocyanine green fluorescent imaging in surgery. Int J Biomed Imaging 2012, 940585, doi:10.1155/2012/940585 (2012).
15. Parthasarathy, A. B., Chong, S. H., Moscatelli, F. A., Singhal, S. & Yodh, A. G. in SPIE BiOS. 93110X-93110X-93116 (International Society for Optics and Photonics).
16. Simon, J. C. et al. Near-infrared imaging of secondary caries lesions around composite restorations at wavelengths from 1300-1700-nm. Dent Mater 32, 587-595, doi:10.1016/j.dental.2016.01.008 (2016).
17. Chung, S., Fried, D., Staninec, M. & Darling, C. L. Near infrared imaging of teeth at wavelengths between 1200 and 1600 nm. Proc SPIE Int Soc Opt Eng 7884, doi: 10.1117/12.878894 (2011).
18. Li, Z. et al. Endoscopic near-infrared dental imaging with indocyanine green: a pilot study. Ann N Y Acad Sci 1421, 88-96, doi:10.1111/nyas.13674 (2018).
19. Schmidt, F., Dittberner, A., Koscielny, S., Petersen, I. & Guntinas-Lichius, O. Feasibility of real-time near-infrared indocyanine green fluorescence endoscopy for the evaluation of mucosal head and neck lesions. Head Neck 39, 234-240, doi:10.1002/hed.24570 (2017).
20. AV, D. S., Lin, H., Henderson, E. R., Samkoe, K. S. & Pogue, B. W. Review of fluorescence guided surgery systems: identification of key performance capabilities beyond indocyanine green imaging. J Biomed Opt 21, 80901, doi:10.1117/1.JBO.21.8.080901 (2016).
21. Xu, J., Kooby, D., Kairdolf, B. & Nie, S. New horizons in intraoperative diagnostics of cancer in image and spectroscopy guided pancreatic cancer surgery. New Horizons in Clinical Case Reports 1, 2 (2017).
22. Xu, J., Kooby, D. & Nie, S. Nanofluorophore Assisted Fluorescence Image-guided Cancer Surgery. Journal of Medical—Clinical Research & Reviews 2, 1-3 (2018).
23. Boehm, T. K. & Ciancio, S. G. Diode laser activated indocyanine green selectively kills bacteria. J Int Acad Periodontol 13, 58-63 (2011).
24. McNally, K. M., Gillings, B. R. & Dawes, J. M. Dye-assisted diode laser ablation of carious enamel and dentine. Aust Dent J 44, 169-175 (1999).
25. Huang, Z. et al. Endoscopically-assisted operations in the treatment of odontogenic peripheral osteomyelitis of the posterior mandible. Br J Oral Maxillofac Surg 54, 542-546, doi:10.1016/j.bjoms.2016.02.023 (2016).
26. Li, Z. et al. Cover Image, Volume 1421, Issue 1. Annals of the New York Academy of Sciences 1421, i-i (2018).
27. Wise, G. & Fan, W. Changes in the tartrate-resistant acid phosphatase cell population in dental follicles and bony crypts of rat molars during tooth eruption. Journal of dental research 68, 150-156 (1989).
28. Fleischmannova, J., Matalova, E., Tucker, A. S. & Sharpe, P. T. Mouse models of tooth abnormalities. Eur J Oral Sci 116, 1-10, doi:10.1111/j.1600-0722.2007.00504.x (2008).
29. Bodner, L., Bar-Ziv, J. & Becker, A. Image accuracy of plain film radiography and computerized tomography in assessing morphological abnormality of impacted teeth. American journal of orthodontics and dentofacial orthopedics 120, 623-628 (2001).
30. Lungova, V. et al. Tooth-bone morphogenesis during postnatal stages of mouse first molar development. J Anat 218, 699-716, doi:10.1111/j.1469-7580.2011.01367.x (2011).
31. Smith, A. M., Mancini, M. C. & Nie, S. Bioimaging: second window for in vivo imaging. Nat. Nanotechnol. 4, 710-711 (2009).
32. Frangioni, J. V. In vivo near-infrared fluorescence imaging. Curr. Opin. Chem. Biol. 7, 626-634 (2003).
33. Schaafsma, B. E. et al. The clinical use of indocyanine green as a near-infrared fluorescent contrast agent for image-guided oncologic surgery. J Surg Oncol 104, 323-332, doi:10.1002/jso.21943 (2011).
34. Plante, M. et al. Sentinel node mapping with indocyanine green and endoscopic near-infrared fluorescence imaging in endometrial cancer. A pilot study and review of the literature. Gynecol Oncol 137, 443-447, doi: 10.1016/j.ygyno.2015.03.004 (2015).
35. Desmettre, T., Devoisselle, J. & Mordon, S. Fluorescence properties and metabolic features of indocyanine green (ICG) as related to angiography. Survey of ophthalmology 45, 15-27 (2000).
36. Kochubey, V., Kulyabina, T., Tuchin, V. & Altshuler, G. Spectral characteristics of indocyanine green upon its interaction with biological tissues. Optics and Spectroscopy 99, 560-566 (2005).
37. Santos Junior, V. E. D., Targino, A. C. D. L., Alencar Filho, A. V. d. & Rosenblatt, A. Are there hidden caries or is this another limitation of the diagnostic conventional exams. Revista Odonto Ciência 30, 45, doi:10.15448/1980-6523.2015.2.14592 (2015).
38. Lin-P'ing Choo-Smith, C., Dong, C., Cleghorn, B. & Hewko, M. Shedding new light on early caries detection. Journal (Canadian Dental Association) 74, 913 (2008).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A near-infrared fluorescence endoscopic dental imaging system, comprising:
    an endoscope forming a plurality of lumens therein;
    a spectrometer optically coupled to a first lumen of the endoscope;
    a near-infrared camera optically coupled to a second lumen of the endoscope;
    a data processor in communication with the spectrometer and the near-infrared camera;
    a bifurcated fiber disposed in the second lumen, the bifurcated fiber having a first channel optically coupled to the spectrometer and a second channel optically coupled to a near-infrared illumination source; and
    a display system in communication with the data processor,
    wherein the near-infrared camera is configured to capture a near-infrared two-dimensional dental image of a specimen having indocyanine green (ICG) and transmit the near-infrared two-dimensional dental image to the data processor,
    wherein the spectrometer is configured to capture fluorescent light from the specimen having the indocyanine green (ICG) and provide a spectroscopic signal to the data processor,
    wherein the display system is configured to communicate with the data processor to receive the near-infrared two-dimensional dental image and the spectroscopic signal and to display a two-dimensional dental image of the specimen,
    wherein the near-infrared two-dimensional dental image of the specimen captured by the near-infrared camera provides an overview of a wide angle imaging field of the specimen and the fluorescent light from the specimen captured by the spectrometer provides a wavelength-resolved spectroscopy of a selected imaged area within the near-infrared two-dimensional dental image, and
    wherein the near-infrared camera has a spatial resolution less than 100 mm in near-infrared.

2. The near-infrared fluorescence endoscopic dental imaging system of claim 1, wherein the near-infrared fluorescence endoscopic dental imaging system does not use ionizing-radiation materials.

3. The near-infrared fluorescence endoscopic dental imaging system of claim 1, further comprising a near-infrared illumination source optically coupled to the first lumen of the endoscope.

4. The near-infrared fluorescence endoscopic dental imaging system of claim 3, wherein the near-infrared illumination source comprises a laser diode.

5. The near-infrared fluorescence endoscopic dental imaging system of claim 3, wherein the near-infrared illumination source comprises a light emitting diode (LED).

6. The near-infrared fluorescence endoscopic dental imaging system according to claim 1,
wherein the near-infrared camera is further configured to capture a two-dimensional dental video, and
wherein the display system is configured to display the two-dimensional dental video in real time.

7. A method for near-infrared fluorescence endoscopic dental imaging using a near-infrared fluorescence endoscopic dental imaging system comprising an endoscope forming a plurality of lumens therein, a spectrometer optically coupled to a first lumen of the endoscope, a near-infrared camera optically coupled to a second lumen of the endoscope, and a bifurcated fiber disposed in the second lumen, the bifurcated fiber having a first channel optically coupled to the spectrometer and a second channel optically coupled to a near-infrared illumination source, the method comprising:
administering a near-infrared fluorescent dye to a subject, the near-infrared fluorescent dye comprising indocyanine green (ICG);
waiting a predetermined period of time;
observing in a predetermined imaging window of time;
illuminating selected dental tissue of the subject with near-infrared light from the near-infrared illumination source through the second channel optically coupled to the near-infrared illumination source;
capturing a two-dimensional near-infrared dental image of the subject using the near-infrared camera to provide an overview of a wide angle imaging field of the selected dental tissue of the subject, the near-infrared camera having a spatial resolution less than 100 mm in near-infrared;
capturing near-infrared light from the selected tissue of subject using the spectrometer through the first channel optically coupled to the spectrometer to provide a wavelength-resolved spectroscopy of a selected imaged area within the near-infrared two-dimensional dental image;
analyzing the near-infrared light to create a spectroscopic signal; and
displaying a two-dimensional near-infrared dental image.

8. The method of claim 7, further comprising displaying spectroscopic data corresponding to the spectroscopic signal.

9. The method of claim 7, wherein the method does not use ionizing-radiation materials.

10. The method according to claim 7, further comprising:
capturing a two-dimensional near-infrared dental movie of the dental tissue of the subject; and
displaying the two-dimensional near-infrared dental movie of the selected dental tissue of the subject in real time.

11. The method according to claim 7, further comprising analyzing the spectroscopic signal to identify one of inflammation or disease in the selected dental tissue.

12. A near-infrared dental imaging system, comprising:
a bifurcated optical fiber adapted to be disposed in a first lumen of an endoscope;
a spectrometer optically coupled to a first channel of the bifurcated optical fiber;
a near-infrared camera optically coupled to a second lumen of the endoscope;
a near-infrared illumination source optically coupled to a second channel of the bifurcated optical fiber; and
a data processor in communication with the spectrometer and the near-infrared camera;
wherein the bifurcated optical fiber is configured to receive fluorescent light from a specimen having indocyanine green (ICG) into the first channel and transmit the fluorescent light to the spectrometer,
wherein the spectrometer is configured to detect the fluorescent light from the bifurcated optical fiber and provide a spectroscopic signal to the data processor,
wherein the near-infrared camera is configured to receive near-infrared light from the second lumen of the endoscope and capture a near-infrared two-dimensional dental image of the specimen,
wherein the near-infrared camera is further configured to transmit the near-infrared two-dimensional dental image to the data processor,
wherein the data processor is configured to communicate with a display system to display a two-dimensional dental image of the specimen,
wherein the near-infrared two-dimensional dental image of the specimen captured by the near-infrared camera provides an overview of a wide field imaging field of the specimen and the fluorescent light from the specimen detected by the spectrometer provides a wavelength-resolved spectroscopy of a selected imaged area within the near-infrared two-dimensional dental image, and
wherein the near-infrared camera has a spatial resolution less than 100 mm in near-infrared.

13. The near-infrared dental imaging system of claim 12, wherein the near-infrared dental imaging system does not use ionizing-radiation materials.

14. The near-infrared dental imaging system of claim 12, wherein the near-infrared illumination source comprises a laser diode.

15. The near-infrared dental imaging system of claim 12, wherein the near-infrared illumination source comprises a light emitting diode (LED).

16. The near-infrared dental imaging system according to claim 12,
wherein the near-infrared camera is further configured to capture a two-dimensional dental video, and
wherein the data processor is configured to communicate with the display system to display the two-dimensional dental video in real time.

17. The near-infrared dental imaging system according to claim 12, further comprising a display system in communication with the data processor, wherein the data processor is configured to communicate with the display system to display a two-dimensional dental image of the specimen.

18. The near-infrared dental imaging system according to claim 12, further comprising an endoscope,
wherein the bifurcated optical fiber is disposed in a first lumen of the endoscope; and
wherein the near-infrared camera is optically coupled to a second lumen of the endoscope.

* * * * *

UNITED STATES PATENT AND TRADEMARK OFFICE
CERTIFICATE OF CORRECTION

| | | |
|---|---|---|
| PATENT NO. | : 11,925,308 B2 | Page 1 of 1 |
| APPLICATION NO. | : 16/965580 | |
| DATED | : March 12, 2024 | |
| INVENTOR(S) | : Xu et al. | |

It is certified that error appears in the above-identified patent and that said Letters Patent is hereby corrected as shown below:

In the Claims

Column 24, Line 59, "100 mm" should read -- 100 µm --;

Column 25, Line 37, "100 mm" should read -- 100 µm --;

Column 26, Line 36, "100 mm" should read -- 100 µm --.

Signed and Sealed this
Third Day of September, 2024

*Katherine Kelly Vidal*

Katherine Kelly Vidal
*Director of the United States Patent and Trademark Office*